US007323338B2

United States Patent

(12) United States Patent
Amir

(10) Patent No.: US 7,323,338 B2
(45) Date of Patent: Jan. 29, 2008

(54) PLANTS CHARACTERIZED BY AN INCREASED CONTENT OF METHIONINE AND RELATED METABOLITES, METHODS OF GENERATING SAME AND USES THEREOF

(75) Inventor: Rachel Amir, Upper Galilee (IL)

(73) Assignee: Gavish-Galilee Bio Applications Ltd., Kiryat-Shmona (IL)

(*) Notice: Subject to any disclaimer, the term of this patent is extended or adjusted under 35 U.S.C. 154(b) by 348 days.

(21) Appl. No.: 10/475,852

(22) PCT Filed: Apr. 30, 2002

(86) PCT No.: PCT/IL02/00335

§ 371 (c)(1), (2), (4) Date: Nov. 3, 2003

(87) PCT Pub. No.: WO02/088301

PCT Pub. Date: Nov. 7, 2002

(65) Prior Publication Data

US 2006/0107342 A1 May 18, 2006

(51) Int. Cl.
*C12N 15/82* (2006.01)
*C07H 21/04* (2006.01)

(52) U.S. Cl. ...................................... 435/468; 536/23.6

(58) Field of Classification Search ..................... None
See application file for complete search history.

(56) References Cited

U.S. PATENT DOCUMENTS

| | | | |
|---|---|---|---|
| 5,912,414 | A | 6/1999 | Falco et al. |
| 6,127,600 | A | 10/2000 | Beach et al. |
| 2004/0142215 | A1 | 7/2004 | Barbir et al. |

FOREIGN PATENT DOCUMENTS

| | | |
|---|---|---|
| EP | 0485970 | 5/1992 |
| WO | WO 95/31554 | 11/1995 |

OTHER PUBLICATIONS

Kim J. et al. Cloning and analysis of the gene for cystathionine gamma-synthase from *Arabidopsis thaliana*. Plant Mol Biol. Dec. 1996;32(6):1117-24.*

Chiba et al. 1999, Science 286:1371-1374.*

Berrocal-Lobo et al. 2002, Plant J 29:23-32.*

Inaba et al. 1994, Plant Physiol. 104:881-887.*

Shaul et al, "Threonine Overproduction in Transgenic Tobacco Plants Expressing a Mutant Desensitized Asparate Kinase of *Escherichia coli", Plant Physiol.*, 10:1157-1163, 1992.

Galili, G., "Regulation of Lysine and Threonine Synthesis", *The Plant Cell*, 7:89-906, 1995.

Bartlem et al, "Mutation in the Threonine Synthase Gene Results in an Over-Accumulation of Soluble Methionine in *Arabidopsis", Plant Physiol.*, 123:101-110, 2000.

Kim et al, "Repression of Cystathionine γ-Synthase in *Arabidopsis thaliana* Produces Partial Methionine Auxotrophy and Developmental Abnormalities", *Plant Science*, 151:9-18, 2000.

Chiba et al, "Evidence for Autoregulation of Cystathionine γ-Synthase mRNA Stability in *Arabidopsis*", Science, 286:1371-1374, 1999.

Belbahri et al, "Diferent Expression of an *S*-Adenosylmethionine Synthetase Gene in Transgenic Tobacco Callus Modifies Alkaloid Biosynthesis", *Biotechnology and Bioengineering*, 69(1):11-20, 2000.

Pimenta et al, "*S*-Adenosyl-L-Methionine:L-Methionine *S*-methyltransferase From Germinating Barley", *Plant Physiol.*, 118:431-438, 1998.

Thompson et al, "Methionine Synthesis in *Lemna*; Inhibition of Cystathionine γ-Synthase By Propargylglycine", *Plant Physiol.*, 70:1347-1352, 1982.

Datko et al, "Methionine Biosynthesis in *Lemna*: Inhibitor Studies", *Plant Physiol.*, 69:1070-1076, 1982.

Tang et al, "A Novel Composite Locus of *Arabidopsis* Encoding Two Polypeptides with Metatabolically Related But Distinct Functions in Lysine Catabolism", *The Plant Journal*, 23(2):195-203, 2000.

Karchi et al, "Seed-Specific Expression of a Bacterial Desensitized Aspartate Kinase Increases the Production of Seed Threonine and Methionine in Transgenic Tobacco", *The Plant Journal*, 3(5):721-727, 1993.

Ominato et al, "Identification of a Short Highly Conserved Amino Acid Sequence as the Functional Region Required for Post-transcriptional Autoregulation of the Cystathionine γ-Synthase Gene in *Arabidopsis", J. Biological Chemistry*, 277(39):36380-36386, 2002.

Hacham et al, "The N-Terminal Region of *Arabidopsis* Cystathionine γ-Synthase Plays and Important Regulatory role in Methionine Metabolism", *Plant Physiol.*, 128:454-462, 2002.

Anderson, JW, "Sulfur Metabolism in Plants", Chapter 8 in: *The Biochemistry of Plants*, vol. 16, p. 327-381, Academic Press, 1990.

* cited by examiner

*Primary Examiner*—Ashwin Mehta
*Assistant Examiner*—Li Zheng

(57) ABSTRACT

A method of increasing methionine and/or methionine related metabolites in a plant is provided. The method is effected by expressing within the plant a cystathionine γ-synthase encoded by a polynucleotide mutated in, or lacking, a region encoding an N-terminal portion of said cystathionine γ-synthase, said region being functional in downregulating an activity of said cystathionine γ-synthase in the plant.

6 Claims, 10 Drawing Sheets

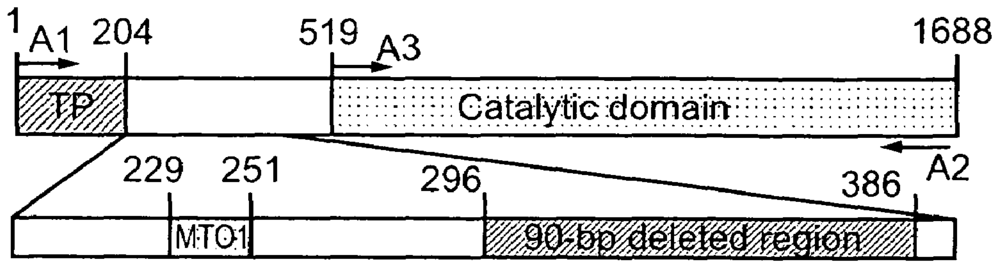
Fig. 2
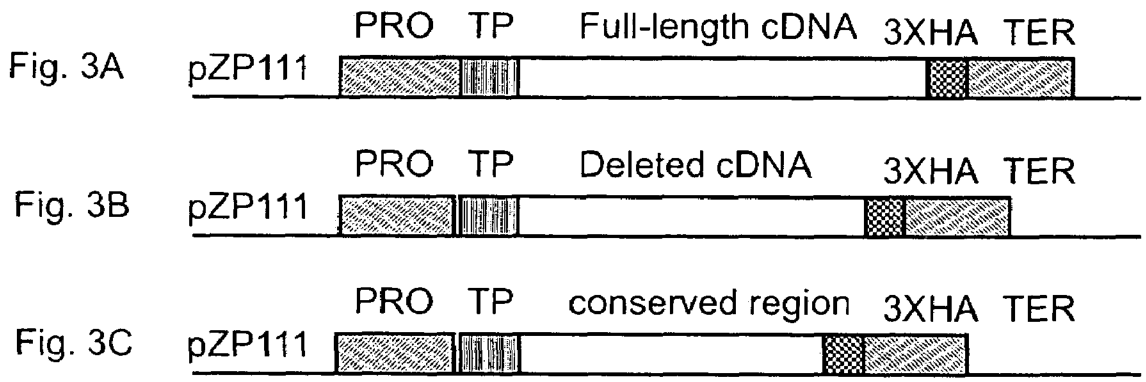

```
Aarbidopsis    1  MAVSSFQCPTIFSSSSISGFQCRSDPDLVGSPVGGSSRRRVHASAGIS SFTGD GL  SR                 I  R
Soybean        1  ---------MAVSSSHMPFTFFCRSDFDFSPFPFSFDWLRRRNFRSSAD GAAFH -I SL                 T  P
Zea            1  ------------------------------MATVSLTPGAVF TESGG LA AT                        I  R
Helicobacter   1  ---------------------------------------------------------------------------
Escherichia    1  ---------------------------------------------------------------------------

Aarbidopsis    81 S G      K NNPSSALPSAAAAAATSSASAVSSAAS AASSA A PVA APPVVLKSVDEEVV AESGIREKIG
Soybean        72 S G      S N-------SD--NSP---------AA PAPPA T TDA IVPLPVVVAANEDV VSAAADENGA
Zea            45 S G        DCP----AAR--PHLG---------- GRRAR V SSH AAASAAAAASAAAE SAIPNARVAQ
Helicobacter   1  ---------------------------------------------------------------------------
Escherichia    1  ---------------------------------------------------------------------------

Aarbidopsis    161 SVQLTDSKHSF SSEGSL HA ERLGF G VEA TTPVNTSAY KK AE LIDFREKPSV EYGRYGNPT V E
Soybean        134 VQLNSSSYESE KSL SK HA ERLGF Q ETG TTPVNTSAY KK AE LIDFKENPQV EYGRYGNPT V E
Zea            108 PSAVVLARRHL GSF SL A HA EPLGPR ATDA TTPVNTSAY NNSQ ELIDFREG HAE EYGRYGNPT EA K
Helicobacter   1  ----------MRMQ KL HE--GI SEDAT G A SVP YG ST RQDAIG ------- HKGV EYS GNPT RFA  L
Escherichia    1  ----------M RKQA E AVRSGL NDDEQYGC VPP HLS T N TGFN------- EPR H TS RGNP RD  RA

Aarbidopsis    241 ISALEGAESTLVHASGM C STV LLALVPAGGH VTTTDCYRKTRI  NF PR G  VTVIDPAD A LEA NEFKVS
Soybean        214 TSALEGAESTV MASG C SV LFMALVPAGGH VTTTDCYRKTRI    PR GI TT VIDPAD G LES  EQH VS
Zea            188  SALEK AESTV ASGM Y AAAAY L A PAGGH VTTTDCYRKTRI  NE DP PR G SMTVI PAD DA QN  IDNNNVS
Helicobacter   59   D EGG VKGFAF ASG A I HA  SL Q- G D  LGD V GG FRLFNQV V NG L SC  E TS D SQ KK   KP- TK
Escherichia    61             TN  G   I H  T  VF KPGDL  APH D GC YRLF  LAK GCYR LF  Q  EQ  IRA  AE- KPK

Aarbidopsis    321 LFFTESPTNPFLRCVD  L VSK  CH K GT  C II GTFATP NQKALALGAD LV HS TRY GGHN V AGC C S- LK V
Soybean        294 LFFTESPTNPFLRCVD KL VSE CH K GT  C II GTFATP NQKALALGAD L HSL TRY GGH H  GC LSGS- IK
Zea            268 LFFTE PTNPFLRC D EHVSN CH SK AD  CI S TFA  E NQKAL TLGADVH HS TRY EGHN V GGC V GR- DE
Helicobacter   137 AL L   N L  IT  AQC S  D GL TI  N FATE YY NP  LGA  VA H  TRY GGHS DV  GL   TNNEA  A
Escherichia    140  VLVES  N   VVD AKI CH  A EV GA SV  N  LS AL NP  ALGAD V HSC  RY NGHS DV AGV I KDPD

Aarbidopsis    400 SE PNL  HV GGTLNPHAAY  T RGMKTLHLRVCQQNS TA  MA EI LFA HPKV S VYYPGLPSHPFHF LARRQ NTG GGV
Soybean        373 S  RTLH HV GGTLNPHAAY  L RGMKTLHLRVCQQNS G  RMKL  EA HPKV KRVYYPGLPSHPEH LAKR NTG GGV
Zea            347 SK P K HHV GGV LNPHAAY  I  RGMKTLHLRVCQ NN  F  RMA Q  EEH P A VERVYYPGLP SH PEH H A RS Q TG GGV
Helicobacter   217 Q   AF  ONA GG V  G C DS    IRG   KT     ICV E  L  KH P  LP  ERVY PG P     NY  LA   Q RG S
Escherichia    220   LAW  AN N  GV GG AFDS  LI RGL T  VPR  LA RN Q A VK  TQ    K   SL  ENQG    ARGQK FG M

Aarbidopsis    480 VSFE DGI I   N  DS LKI PY  PS FGG CES IVDQPAIMSYW  Q E L KYG  DNLVRFS GVEDF D R D  Q
Soybean        453 VSFE DGILH    LASF GGCES IV DQPAI SYW  QSE AK    DNL VRFS  GVEDF EDL RAD  Q
Zea            427 VSFE AGDF A RF DS R PY  PSFGGCESI DQPAIMSYW S K  DI YG  DNL RFS GVEDFEDL ND  QA
Helicobacter   297  SFT  KN  S  ALA   DS  N F P  SLGGVES  GIPA  HACS  KTQ EAA G  GLVS  S VC   HE  DLL EDLE QA
Escherichia    300  SFE  DGI EQ LR   GG S FT  ES LGGVES SHA T  HAG  AP ARAA GF T L  I GT  EDGEDI ADL  G

Aarbidopsis    560 LEA ---
Soybean        533 LEA ---
Zea            506 L  ---
Helicobacter   376 FAK G--
Escherichia    380 FR ANKG
```

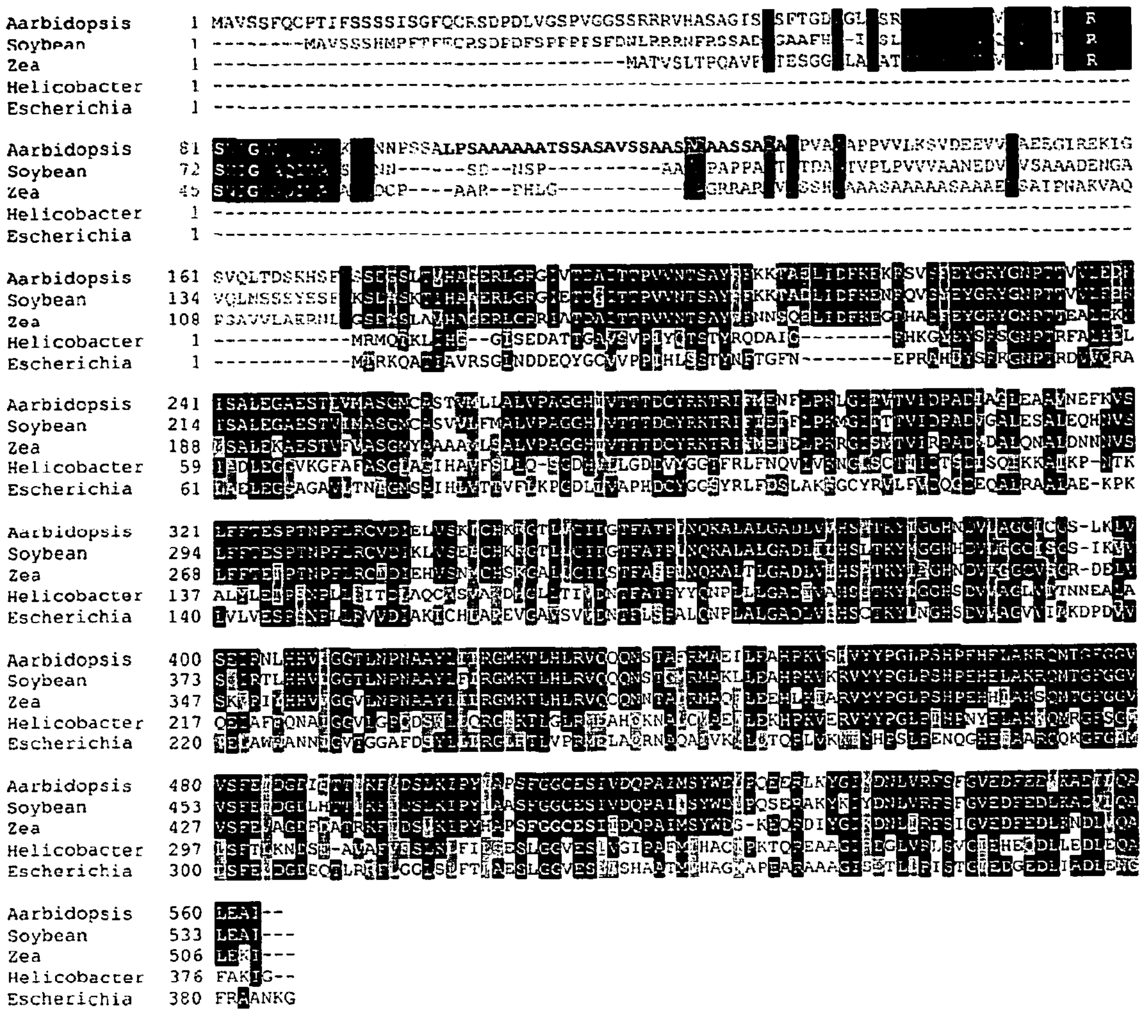

Fig. 4

ATGGCCGTCTCATCATTCCAGTGCCCTACCATCTTCTCCTCCTCCTCAATCTCCGGCTTT
CAATGCCGTTCTGATCCAGATCTCGTCGGTTCTCCCGTCGGTGGATCATCTCGCCGTCGT
GTCCATGCCTCCGCCGGGATTTCTTCCTCATTCACCGGGGACGCTGGATTATCCTCCAGG
ATCTTAAGATTTCCTCCTAATTTCGTCCGTCAGCTGAGCATTAAAGCCCGTAGAAACTGT
AGCAACATCGGTGTTGCACAGATCGTGGCGGCTAAGTGGTCCAACAACCCATCCTCCGCG
TTACCTTCGGCGGCGGCGGCTGCTGCTACCTCGTCTGCATCTGCGGTTTCTTCCGCCGCA
TCTGCAGCCGCAGCCTCGTCCGCCGCCGCCGCCCCTGTGGCTGCCGCGCCTCCCGTCGTG
CTGAAAAGCGTCGATGAGGAGGTTGTGGTGGCCGAGGAGGGGATCAGGGAGAAGATAGGT
AGTGTACAGCTGACGGATTCCAAACATTCTTTCTTGAGCTCCGATGGGAGCCTCACTGTT
CATGCCGGTGAAAGATTAGGCCGTGGTATAGTGACGGATGCTATCACTACTCCTGTAGTC
AACACATCTGCCTACTTCTTCAAGAAAACTGCTGAGCTTATTGACTTCAAGGAGAAAAGG
AGTGTGAGTTTCGAGTATGGTCGTTATGGTAACCCTACGACTGTGGTACTTGAAGATAAG
ATAAGTGCACTTGAAGGGGCTGAATCAACTTTGGTTATGGCATCTGGGATGTGTGCAAGC
ACTGTTATGCTTTTGGCATTGGTTCCTGCTGGTGGACACATTGTCACTACTACTGATTGC
TACAGGAAGACTAGGATCTTCATGGAGAATTTTCTTCCCAAGTTGGGGATCACTGTCACT
GTGATTGATCCTGCTGATATCGCAGGGCTTGAAGCTGCAGTGAATGAGTTCAAGGTATCT
CTGTTCTTCACTGAGTCCCCGACAAACCCATTCCTTAGATGTGTCGACATTGAGCTAGTT
TCAAAAATATGCCACAAGAGGGGAACTCTGGTTTGCATTGATGGCACCTTTGCAACACCT
CTGAATCAGAAAGCCCTTGCTCTTGGTGCTGATCTTGTCGTGCACTCTGCTACAAAGTAC
ATTGGAGGACACAATGATGTTCTTGCTGGATGCATCTGTGGTTCACTGAAGTTGGTTTCA
GAAATTCGCAATCTGCATCATGTGTTGGGAGGAACACTTAACCCAAACGCTGCGTACCTA
ATCATCCGAGGCATGAAGACATTGCATCTTCGTGTACAGCAACAGAATTCGACCGCTTTT
AGAATGGCCGAAATTTTAGAGGCACATCCTAAGGTGAGTCATGTGTACTATCCAGGCCTT
CCAAGTCATCCCGAACATGAACTCGCCAAGCGACAAATGACTGGTTTTGGAGGTGTGGTC
AGTTTCGAGATTGATGGAGACATTGAAACGACAATCAAGTTTGTGGATTCTCTAAAGATT
CCTTACATTGCACCATCCTTCGGTGGCTGCGAAAGCATTGTTGACCAACCTGCTATCATG
TCCTACTGGGATCTGCCGCAAGAGGAGAGACTAAAGTATGGAATCAAAGATAACTTGGTT
CGTTTCAGCTTTGGAGTTGAAGACTTTGAAGATGTCAAAGCTGACATTCTTCAAGCTCTC
GAAGCCATCTGA

Fig. 5a (SEQ ID No: 1)

GTCCGTCAGCTGAGCATTAAAGCCCGTAGAAACTGTAGCAACATCGGTGTTGCACAGATC
GTGGCGGCTAAGTGGTCCAACAACCCATCCTCCGCGTTACCTTCGGCGGCGGCGGCTGCT
GCTACCTCGTCTGCATCTGCGGTTTCTTCCGCCGCATCTGCAGCCGCAGCCTCGTCCGCC
GCCGCCGCCCCTGTGGCTGCCGCGCCTCCCGTCGTGCTGAAAAGCGTCGATGAGGAGGTT
GTGGTGGCCGAGGAGGGGATCAGGGAGAAGATAGGTAGTGTACAGCTGACGGATTCCAAA
CATTCTTTCTTGAGCTCCGATGGGAGCCTCACTGTTCATGCCGGTGAAAGATTAGGCCGT
GGTATAGTGACGGATGCTATCACTACTCCTGTAGTCAACACATCTGCCTACTTCTTCAAG
AAAACTGCTGAGCTTATTGACTTCAAGGAGAAAAGGAGTGTGAGTTTCGAGTATGGTCGT
TATGGTAACCCTACGACTGTGGTACTTGAAGATAAGATAAGTGCACTTGAAGGGGCTGAA
TCAACTTTGGTTATGGCATCTGGGATGTGTGCAAGCACTGTTATGCTTTTGGCATTGGTT
CCTGCTGGTGGACACATTGTCACTACTACTGATTGCTACAGGAAGACTAGGATCTTCATG
GAGAATTTTCTTCCCAAGTTGGGGATCACTGTCACTGTGATTGATCCTGCTGATATCGCA
GGGCTTGAAGCTGCAGTGAATGAGTTCAAGGTATCTCTGTTCTTCACTGAGTCCCCGACA
AACCCATTCCTTAGATGTGTCGACATTGAGCTAGTTTCAAAAATATGCCACAAGAGGGGA
ACTCTGGTTTGCATTGATGGCACCTTTGCAACACCTCTGAATCAGAAAGCCCTTGCTCTT
GGTGCTGATCTTGTCGTGCACTCTGCTACAAAGTACATTGGAGGACACAATGATGTTCTT
GCTGGATGCATCTGTGGTTCACTGAAGTTGGTTTCAGAAATTCGCAATCTGCATCATGTG
TTGGGAGGAACACTTAACCCAAACGCTGCGTACCTAATCATCCGAGGCATGAAGACATTG
CATCTTCGTGTACAGCAACAGAATTCGACCGCTTTTAGAATGGCCGAAATTTTAGAGGCA
CATCCTAAGGTGAGTCATGTGTACTATCCAGGCCTTCCAAGTCATCCCGAACATGAACTC
GCCAAGCGACAAATGACTGGTTTTGGAGGTGTGGTCAGTTTCGAGATTGATGGAGACATT
GAAACGACAATCAAGTTTGTGGATTCTCTAAAGATTCCTTACATTGCACCATCCTTCGGT
GGCTGCGAAAGCATTGTTGACCAACCTGCTATCATGTCCTACTGGGATCTGCCGCAAGAG
GAGAGACTAAAGTATGGAATCAAAGATAACTTGGTTCGTTTCAGCTTTGGAGTTGAAGAC
TTTGAAGATGTCAAAGCTGACATTCTTCAAGCTCTCGAAGCCATCTGA

Fig. 5b (SEQ ID No: 2)

GTCCGTCAGCTGAGCATTAAAGCCCGTAGAAACTGTAGCAACATCGGTGTTGCACAGATC
GTGGCGGCTAAGTGGTCCAACAACCCATCCTCCGCCGCCCCTGTGGCTGCCGCGCCTCCC
GTCGTGCTGAAAAGCGTCGATGAGGAGGTTGTGGTGGCCGAGGAGGGGATCAGGGAGAAG
ATAGGTAGTGTACAGCTGACGGATTCCAAACATTCTTTCTTGAGCTCCGATGGGAGCCTC
ACTGTTCATGCCGGTGAAAGATTAGGCCGTGGTATAGTGACGGATGCTATCACTACTCCT
GTAGTCAACACATCTGCCTACTTCTTCAAGAAAACTGCTGAGCTTATTGACTTCAAGGAG
AAAAGGAGTGTGAGTTTCGAGTATGGTCGTTATGGTAACCCTACGACTGTGGTACTTGAA
GATAAGATAAGTGCACTTGAAGGGGCTGAATCAACTTTGGTTATGGCATCTGGGATGTGT
GCAAGCACTGTTATGCTTTTGGCATTGGTTCCTGCTGGTGGACACATTGTCACTACTACT
GATTGCTACAGGAAGACTAGGATCTTCATGGAGAATTTTCTTCCCAAGTTGGGGATCACT
GTCACTGTGATTGATCCTGCTGATATCGCAGGGCTTGAAGCTGCAGTGAATGAGTTCAAG
GTATCTCTGTTCTTCACTGAGTCCCCGACAAACCCATTCCTTAGATGTGTCGACATTGAG
CTAGTTTCAAAAATATGCCACAAGAGGGGAACTCTGGTTTGCATTGATGGCACCTTTGCA
ACACCTCTGAATCAGAAAGCCCTTGCTCTTGGTGCTGATCTTGTCGTGCACTCTGCTACA
AAGTACATTGGAGGACACAATGATGTTCTTGCTGGATGCATCTGTGGTTCACTGAAGTTG
GTTTCAGAAATTCGCAATCTGCATCATGTGTTGGGAGGAACACTTAACCCAAACGCTGCG
TACCTAATCATCCGAGGCATGAAGACATTGCATCTTCGTGTACAGCAACAGAATTCGACC
GCTTTTAGAATGGCCGAAATTTTAGAGGCACATCCTAAGGTGAGTCATGTGTACTATCCA
GGCCTTCCAAGTCATCCCGAACATGAACTCGCCAAGCGACAAATGACTGGTTTTGGAGGT
GTGGTCAGTTTCGAGATTGATGGAGACATTGAAACGACAATCAAGTTTGTGGATTCTCTA
AAGATTCCTTACATTGCACCATCCTTCGGTGGCTGCGAAAGCATTGTTGACCAACCTGCT
ATCATGTCCTACTGGGATCTGCCGCAAGAGGAGAGACTAAAGTATGGAATCAAAGATAAC
TTGGTTCGTTTCAGCTTTGGAGTTGAAGACTTTGAAGATGTCAAAGCTGACATTCTTCAA
GCTCTCGAAGCCATCTGA

Fig. 5c (SEQ ID No: 3)

AGCTCCGATGGGAGCCTCACTGTTCATGCCGGTGAAAGATTAGGCCGTGGTATAGTGACG
GATGCTATCACTACTCCTGTAGTCAACACATCTGCCTACTTCTTCAAGAAAACTGCTGAG
CTTATTGACTTCAAGGAGAAAAGGAGTGTGAGTTTCGAGTATGGTCGTTATGGTAACCCT
ACGACTGTGGTACTTGAAGATAAGATAAGTGCACTTGAAGGGGCTGAATCAACTTTGGTT
ATGGCATCTGGGATGTGTGCAAGCACTGTTATGCTTTTGGCATTGGTTCCTGCTGGTGGA
CACATTGTCACTACTACTGATTGCTACAGGAAGACTAGGATCTTCATGGAGAATTTTCTT
CCCAAGTTGGGGATCACTGTCACTGTGATTGATCCTGCTGATATCGCAGGGCTTGAAGCT
GCAGTGAATGAGTTCAAGGTATCTCTGTTCTTCACTGAGTCCCCGACAAACCCATTCCTT
AGATGTGTCGACATTGAGCTAGTTTCAAAAATATGCCACAAGAGGGGAACTCTGGTTTGC
ATTGATGGCACCTTTGCAACACCTCTGAATCAGAAAGCCCTTGCTCTTGGTGCTGATCTT
GTCGTGCACTCTGCTACAAAGTACATTGGAGGACACAATGATGTTCTTGCTGGATGCATC
TGTGGTTCACTGAAGTTGGTTTCAGAAATTCGCAATCTGCATCATGTGTTGGGAGGAACA
CTTAACCCAAACGCTGCGTACCTAATCATCCGAGGCATGAAGACATTGCATCTTCGTGTA
CAGCAACAGAATTCGACCGCTTTTAGAATGGCCGAAATTTTAGAGGCACATCCTAAGGTG
AGTCATGTGTACTATCCAGGCCTTCCAAGTCATCCCGAACATGAACTCGCCAAGCGACAA
ATGACTGGTTTTGGAGGTGTGGTCAGTTTCGAGATTGATGGAGACATTGAAACGACAATC
AAGTTTGTGGATTCTCTAAAGATTCCTTACATTGCACCATCCTTCGGTGGCTGCGAAAGC
ATTGTTGACCAACCTGCTATCATGTCCTACTGGGATCTGCCGCAAGAGGAGAGACTAAAG
TATGGAATCAAAGATAACTTGGTTCGTTTCAGCTTTGGAGTTGAAGACTTTGAAGATGTC
AAAGCTGACATTCTTCAAGCTCTCGAAGCCATCTGA

Fig. 5d (SEQ ID No: 4)

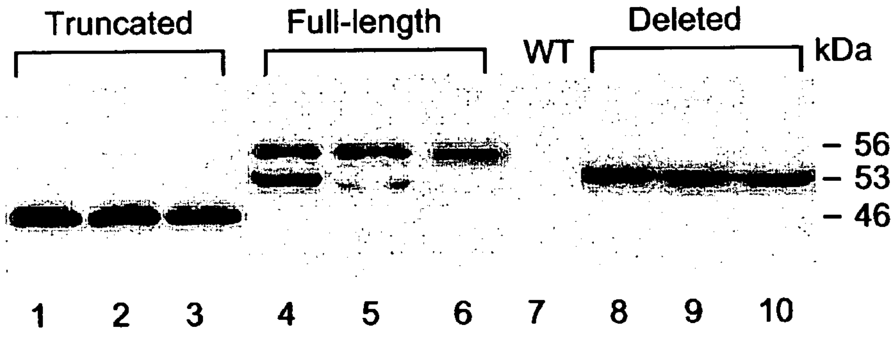

Fig. 6

Bound methionine

SEQUENCE LISTING

```
<160> NUMBER OF SEQ ID NOS: 7

<210> SEQ ID NO 1
<211> LENGTH: 1692
<212> TYPE: DNA
<213> ORGANISM: Arabidopsis thaliana

<400> SEQUENCE: 1

atggccgtct catcattcca gtgccctacc atcttctcct cctcctcaat ctccggcttt     60

caatgccgtt ctgatccaga tctcgtcggt tctcccgtcg gtggatcatc tcgccgtcgt    120

gtccatgcct ccgccgggat ttcttcctca ttcaccgggg acgctggatt atcctccagg    180

atcttaagat ttcctcctaa tttcgtccgt cagctgagca ttaaagcccg tagaaactgt    240

agcaacatcg gtgttgcaca gatcgtggcg gctaagtggt ccaacaaccc atcctccgcg    300

ttaccttcgg cggcggcggc tgctgctacc tcgtctgcat ctgcggtttc ttccgccgca    360

tctgcagccg cagcctcgtc cgccgccgcc gcccctgtgg ctgccgcgcc tcccgtcgtg    420

ctgaaaagcg tcgatgagga ggttgtggtg gccgaggagg ggatcaggga gaagataggt    480

agtgtacagc tgacggattc caaacattct ttcttgagct ccgatgggag cctcactgtt    540

catgccggtg aaagattagg ccgtggtata gtgacggatg ctatcactac tcctgtagtc    600

aacacatctg cctacttctt caagaaaact gctgagctta ttgacttcaa ggagaaaagg    660

agtgtgagtt tcgagtatgg tcgttatggt aaccctacga ctgtggtact tgaagataag    720

ataagtgcac ttgaaggggc tgaatcaact ttggttatgg catctgggat gtgtgcaagc    780

actgttatgc ttttggcatt ggttcctgct ggtggacaca ttgtcactac tactgattgc    840

tacaggaaga ctaggatctt catggagaat tttcttccca agttggggat cactgtcact    900

gtgattgatc ctgctgatat cgcagggctt gaagctgcag tgaatgagtt caaggtatct    960

ctgttcttca ctgagtcccc gacaaaccca ttccttagat gtgtcgacat tgagctagtt   1020

tcaaaaatat gccacaagag gggaactctg gtttgcattg atggcacctt tgcaacacct   1080
```

-continued

```
ctgaatcaga aagcccttgc tcttggtgct gatcttgtcg tgcactctgc tacaaagtac   1140

attggaggac acaatgatgt tcttgctgga tgcatctgtg gttcactgaa gttggtttca   1200

gaaattcgca atctgcatca tgtgttggga ggaacactta acccaaacgc tgcgtaccta   1260

atcatccgag gcatgaagac attgcatctt cgtgtacagc aacagaattc gaccgctttt   1320

agaatggccg aaattttaga ggcacatcct aaggtgagtc atgtgtacta tccaggcctt   1380

ccaagtcatc ccgaacatga actcgccaag cgacaaatga ctggttttgg aggtgtggtc   1440

agtttcgaga ttgatggaga cattgaaacg acaatcaagt ttgtggattc tctaaagatt   1500

ccttacattg caccatcctt cggtggctgc gaaagcattg ttgaccaacc tgctatcatg   1560

tcctactggg atctgccgca agaggagaga ctaaagtatg gaatcaaaga taacttggtt   1620

cgtttcagct ttggagttga agactttgaa gatgtcaaag ctgacattct tcaagctctc   1680

gaagccatct ga                                                         1692
```

<210> SEQ ID NO 2
<211> LENGTH: 1488
<212> TYPE: DNA
<213> ORGANISM: Arabidopsis thaliana

<400> SEQUENCE: 2

```
gtccgtcagc tgagcattaa agcccgtaga aactgtagca acatcggtgt tgcacagatc     60

gtggcggcta agtggtccaa caacccatcc tccgcgttac cttcggcggc ggcggctgct    120

gctacctcgt ctgcatctgc ggtttcttcc gccgcatctg cagccgcagc ctcgtccgcc    180

gccgccgccc ctgtggctgc cgcgcctccc gtcgtgctga aaagcgtcga tgaggaggtt    240

gtggtggccg aggaggggat cagggagaag ataggtagtg tacagctgac ggattccaaa    300

cattctttct tgagctccga tgggagcctc actgttcatg ccggtgaaag attaggccgt    360

ggtatagtga cggatgctat cactactcct gtagtcaaca catctgccta cttcttcaag    420

aaaactgctg agcttattga cttcaaggag aaaaggagtg tgagtttcga gtatggtcgt    480

tatggtaacc ctacgactgt ggtacttgaa gataagataa gtgcacttga aggggctgaa    540

tcaactttgg ttatggcatc tgggatgtgt gcaagcactg ttatgctttt ggcattggtt    600

cctgctggtg gacacattgt cactactact gattgctaca ggaagactag gatcttcatg    660

gagaattttc ttcccaagtt ggggatcact gtcactgtga ttgatcctgc tgatatcgca    720

gggcttgaag ctgcagtgaa tgagttcaag gtatctctgt tcttcactga gtccccgaca    780

aacccattcc ttagatgtgt cgacattgag ctagtttcaa aaatatgcca caagagggga    840

actctggttt gcattgatgg cacctttgca acacctctga atcagaaagc ccttgctctt    900

ggtgctgatc ttgtcgtgca ctctgctaca aagtacattg gaggacacaa tgatgttctt    960

gctggatgca tctgtggttc actgaagttg gtttcagaaa ttcgcaatct gcatcatgtg   1020

ttgggaggaa cacttaaccc aaacgctgcg tacctaatca tccgaggcat gaagacattg   1080

catcttcgtg tacagcaaca gaattcgacc gcttttagaa tggccgaaat tttagaggca   1140

catcctaagg tgagtcatgt gtactatcca ggccttccaa gtcatcccga acatgaactc   1200

gccaagcgac aaatgactgg ttttggaggt gtggtcagtt tcgagattga tggagacatt   1260

gaaacgacaa tcaagtttgt ggattctcta aagattcctt acattgcacc atccttcggt   1320

ggctgcgaaa gcattgttga ccaacctgct atcatgtcct actgggatct gccgcaagag   1380

gagagactaa agtatggaat caaagataac ttggttcgtt tcagctttgg agttgaagac   1440

tttgaagatg tcaaagctga cattcttcaa gctctcgaag ccatctga                 1488
```

-continued

<210> SEQ ID NO 3
<211> LENGTH: 1398
<212> TYPE: DNA
<213> ORGANISM: Arabidopsis thaliana

<400> SEQUENCE: 3
gtccgtcagc tgagcattaa agcccgtaga aactgtagca acatcggtgt tgcacagatc 60
gtggcggcta agtggtccaa caacccatcc tccgccgccc ctgtggctgc cgcgcctccc 120
gtcgtgctga aaagcgtcga tgaggaggtt gtggtggccg aggaggggat cagggagaag 180
ataggtagtg tacagctgac ggattccaaa cattctttct tgagctccga tgggagcctc 240
actgttcatg ccggtgaaag attaggccgt ggtatagtga cggatgctat cactactcct 300
gtagtcaaca catctgccta cttcttcaag aaaactgctg agcttattga cttcaaggag 360
aaaaggagtg tgagtttcga gtatggtcgt tatggtaacc ctacgactgt ggtacttgaa 420
gataagataa gtgcacttga aggggctgaa tcaactttgg ttatggcatc tgggatgtgt 480
gcaagcactg ttatgctttt ggcattggtt cctgctggtg gacacattgt cactactact 540
gattgctaca ggaagactag gatcttcatg gagaattttc ttcccaagtt ggggatcact 600
gtcactgtga ttgatcctgc tgatatcgca gggcttgaag ctgcagtgaa tgagttcaag 660
gtatctctgt tcttcactga gtccccgaca aacccattcc ttagatgtgt cgacattgag 720
ctagtttcaa aaatatgcca caagagggga actctggttt gcattgatgg cacctttgca 780
acacctctga atcagaaagc ccttgctctt ggtgctgatc ttgtcgtgca ctctgctaca 840
aagtacattg gaggacacaa tgatgttctt gctggatgca tctgtggttc actgaagttg 900
gtttcagaaa ttcgcaatct gcatcatgtg ttgggaggaa cacttaaccc aaacgctgcg 960
tacctaatca tccgaggcat gaagacattg catcttcgtg tacagcaaca gaattcgacc 1020
gcttttagaa tggccgaaat tttagaggca catcctaagg tgagtcatgt gtactatcca 1080
ggccttccaa gtcatcccga acatgaactc gccaagcgac aaatgactgg ttttggaggt 1140
gtggtcagtt tcgagattga tggagacatt gaaacgacaa tcaagtttgt ggattctcta 1200
aagattcctt acattgcacc atccttcggt ggctgcgaaa gcattgttga ccaacctgct 1260
atcatgtcct actgggatct gccgcaagag gagagactaa agtatggaat caaagataac 1320
ttggttcgtt tcagctttgg agttgaagac tttgaagatg tcaaagctga cattcttcaa 1380
gctctcgaag ccatctga 1398

<210> SEQ ID NO 4
<211> LENGTH: 1176
<212> TYPE: DNA
<213> ORGANISM: Arabidopsis thaliana

<400> SEQUENCE: 4
agctccgatg ggagcctcac tgttcatgcc ggtgaaagat taggccgtgg tatagtgacg 60
gatgctatca ctactcctgt agtcaacaca tctgcctact tcttcaagaa aactgctgag 120
cttattgact tcaaggagaa aaggagtgtg agtttcgagt atggtcgtta tggtaaccct 180
acgactgtgg tacttgaaga taagataagt gcacttgaag gggctgaatc aactttggtt 240
atggcatctg ggatgtgtgc aagcactgtt atgcttttgg cattggttcc tgctggtgga 300
cacattgtca ctactactga ttgctacagg aagactagga tcttcatgga gaattttctt 360
cccaagttgg ggatcactgt cactgtgatt gatcctgctg atatcgcagg gcttgaagct 420

-continued

```
gcagtgaatg agttcaaggt atctctgttc ttcactgagt ccccgacaaa cccattcctt    480

agatgtgtcg acattgagct agtttcaaaa atatgccaca agaggggaac tctggtttgc    540

attgatggca cctttgcaac acctctgaat cagaaagccc ttgctcttgg tgctgatctt    600

gtcgtgcact ctgctacaaa gtacattgga ggacacaatg atgttcttgc tggatgcatc    660

tgtggttcac tgaagttggt ttcagaaatt cgcaatctgc atcatgtgtt gggaggaaca    720

cttaacccaa acgctgcgta cctaatcatc cgaggcatga agacattgca tcttcgtgta    780

cagcaacaga attcgaccgc ttttagaatg gccgaaattt tagaggcaca tcctaaggtg    840

agtcatgtgt actatccagg ccttccaagt catcccgaac atgaactcgc caagcgacaa    900

atgactggtt ttggaggtgt ggtcagtttc gagattgatg gagacattga aacgacaatc    960

aagtttgtgg attctctaaa gattccttac attgcaccat ccttcggtgg ctgcgaaagc   1020

attgttgacc aacctgctat catgtcctac tgggatctgc cgcaagagga gagactaaag   1080

tatggaatca aagataactt ggttcgtttc agctttggag ttgaagactt tgaagatgtc   1140

aaagctgaca ttcttcaagc tctcgaagcc atctga                             1176


<210> SEQ ID NO 5
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 5

agcatgctcg tccgtcagct gagcattaaa gc                                   32


<210> SEQ ID NO 6
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 6

acccggggat gggcttcgag agcttgaag                                       29


<210> SEQ ID NO 7
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 7

agcatgctca gctccgatgg gagcctcact g                                    31
```

PLANTS CHARACTERIZED BY AN INCREASED CONTENT OF METHIONINE AND RELATED METABOLITES, METHODS OF GENERATING SAME AND USES THEREOF

FIELD AND BACKGROUND OF THE INVENTION

The present invention relates to a plants characterized by an increased content of methionine and methionine related metabolites, to methods of generating same and to uses thereof.

The diets of humans and livestock largely consists of plant material which contains low amounts of several essential amino acids not naturally synthesized by animals or humans. As a result, the nutritional value of plant material and as such plant derived foodstuff is typically limited, oftentimes requiring supplementation of plant derived foodstuff with synthetic amino acids in order to increase it's nutritional value.

Efforts to improve the balance of essential amino acids in the seed proteins of important crops utilizing classical breeding and mutant selection have met with limited success on the laboratory scale and failure on a commercial scale as agronomically acceptable cultivars have not yet been produced.

One of the most important essential amino acid, methionine, exists in limited quantities in legumes, cereals and other crops (Andersen J W., "The Biochemistry of Plants", Academic Press, NY, 1990, pp. 327-381).

The level of free methionine in plants is very low both in vegetative tissues and seeds. Methionine levels are regulated by both rate of synthesis and metabolism into derivative compounds. Methionine has a short half-life due to rapid conversion to SAM and incorporation into newly synthesized proteins. The incorporation of sulfate, methyl and carbon into methionine and its metabolites has been analyzed in Lemna via tracer elements. It has been observed that methionine is converted into SAM at a rate which is four-folds faster than the incorporation of methionine into proteins (Giovanelli et al., Plant Physiol. 1985, 78:555).

Methionine biosynthesis is subject to regulatory control via cystathionine γ-synthase (CGS), the first enzyme in the Methionine biosynthesis pathway (FIGS. 1*a-b*). Studies conducted in Lemna have shown that the level of CGS activity decreases in plants grown in the presence of exogenous methionine (Thompson et al., Plant Physiol. 1982, 69:1077). Conversely, treatments that induce methionine deprivation resulted in an increase in the steady-state levels of CGS (Thompson et al., Plant Physiol. 1982, 70:1347).

Thus, it was theorized that methionine may regulate its own synthesis through negative feedback control of cystathionine synthesis. Analysis of *Arabidopsis* mto1 mutants that over accumulate soluble methionine (Met) revealed that the gene encoding cystathionine gamma-synthase (CGS), the key enzyme in Met biosynthesis, is regulated at the level of mRNA stability and that an amino acid sequence encoded by the first exon of CGS acts in cis to destabilize its own mRNA in a process that is activated by Met or one of its metabolites. The mto1 mutations were shown to be clustered within a small region in the exon, termed mto1, located downstream of the initiator codon (Chiba et al. Science 1999, 286:1371).

Methionine synthesis is also regulated in the biosynthetic pathway of the aspartate family amino acids at the point of competition between threonine synthase (TS) and CGS for their common substrate O-phosphohomoserine (OPH) (FIGS. 1*a-b*). Evidence for TS-CGS competition and its role in methionine synthesis has been obtained. It has been observed that the mto2-1 mutant of *Arabidopsis* over-accumulates up to 20-fold more soluble methionine than the wild type plant and displays a marked reduction in threonine levels. The mto2-1 allele carries a point mutation in the TS gene that produces a catalytically impaired enzyme (Bartlem et al. Plant Physiol. 2000, 123:101). Thus, decreased TS activity causes methionine overproduction at the expense of threonine. Furthermore, reducing the level of CGS by antisense methods, which in turn reduce levels of methionine, leads to a seven-fold increase in threonine levels relative to wild-type plants (Kim et al., Plant Science 2000, 151:9). Therefore the levels of both TS and CGS are important in the partitioning of OPH to Met and threonine.

Methionine deficiency in, for example, poultry diets leads to retarded growth, decreased feed conversion efficiency and increased fat content. As such, commercial poultry diets are typically supplemented with synthetic Met (see, for example, U.S. Pat. No. 5,773,052).

In addition, it has been shown that wool growth in sheep and milk production in dairy animals are both limited by the availability of the sulfur amino acids (SAAs) methionine and cysteine (Xu et al., Dairy Sci. 1998, 81:1062).

In attempts to increase the SAA content of seeds, genes encoding SAA-rich proteins from vegetative tissues have been isolated and expressed in seeds under the control of seed-specific regulatory sequences. Such an approach has not resulted in an adequate increase in total target amino acid content in the seed. It has been shown that this and other approaches which attempt to increase SAA content by expression of met-rich proteins are typically limited by the ability of plants to synthesize methionine.

In another approach, genetic engineering methods have been utilized in an attempt to modulate the activity of enzymes catalyzing key steps of relevant biosynthetic pathways (see, for example, European Pat. App. No. 485970).

For example, expression of a mutant form of a bacterial aspartate kinase (AK) which desensitizes negative feed-back inhibition of lysine and threonine production in plants, resulted in a significant overproduction of threonine in vegetative tissue. However, expression of this gene under the control of a seed-specific promoter was shown to raise the levels of methionine content in seeds only three-fold relative to that of wild type plants (Karchi, et al., The Plant J. 1993, 3:721).

Thus, although several approaches have been utilized in efforts to increase the levels of methionine and other essential amino acids in plants, such approaches have failed to produce plants exhibiting a significant increase in methionine levels.

There is thus a widely recognized need for, and it would be highly advantageous to have, a method of increasing the content of methionine and its related metabolites in plants, thereby increasing the nutritional and commercial value of such plants.

SUMMARY OF THE INVENTION

According to one aspect of the present invention there is provided a method of increasing methionine and/or methionine related metabolites in a plant, the method comprising expressing within the plant a cystathionine γ-synthase encoded by a polynucleotide mutated in, or lacking, a region encoding an N-terminal portion of the cystathionine γ-synthase, the region being functional in downregulating an activity of the cystathionine γ-synthase in the plant. According to yet another aspect of the present invention there is provided a method of increasing the commercial and/or nutritional value of a plant comprising expressing within at least a portion of the plant a cystathionine γ-synthase encoded by a polynucleotide mutated in, or lacking, a region encoding an N-terminal portion of the cystathionine γ-synthase, the region being functional in downregulating an activity of the cystathionine γ-synthase in the plant, thereby increasing the level of methionine and/or metabolites of the methionine, hence increasing the commercial and/or nutritional value of the plant.

According to still another aspect of the present invention there is provided a method of generating a crop plant having enhanced nutritional value, the method comprising: (a) obtaining a first plant expressing a cystathionine γ-synthase encoded by a polynucleotide mutated in, or lacking, a region encoding an N-terminal portion of the cystathionine γ-synthase, the region being functional in downregulating an activity of the cystathionine γ-synthase in the plant; (b) crossing the first plant with a second plant expressing methionine-rich storage proteins; and (c) isolating progeny plants which express the cystathionine γ-synthase and the methionine-rich storage proteins to thereby obtain the crop plant having enhanced nutritional value.

According to an additional aspect of the present invention there is provided a method of generating a crop plant having enhanced nutritional value, the method comprising transforming the crop plant with: (a) a first polynucleotide encoding a cystathionine γ-synthase, the first polynucleotide being mutated in, or lacking, a region encoding an N-terminal portion of the cystathionine γ-synthase, the region being functional in downregulating an activity of the cystathionine γ-synthase in the plant; and (b) a second polynucleotide encoding, in an expressible form, at least one methionine-rich storage protein, to thereby obtain the crop plant having enhanced nutritional value.

According to still an additional aspect of the present invention there is provided a method of obtaining at least one methionine related metabolite or derivate, the method comprising (a) obtaining a plant expressing a cystathionine γ-synthase encoded by a polynucleotide mutated in, or lacking, a region encoding an N-terminal portion of the cystathionine γ-synthase, the region being functional in downregulating an activity of the cystathionine γ-synthase in the plant; and (b) extracting at least one methionine related metabolite from the plant.

According to further features in preferred embodiments of the invention described below, the plant expressing the cystathionine γ-synthase also over-expresses feed back insensitive aspartae kinase (AK).

According to still further features in the described preferred embodiments the plant expressing the cystathionine γ-synthase and overexpressing feed back insensitive aspartae kinase (AK) is obtained by crossing a first plant over expressing feed back insensitive aspartae kinase (AK) and a second plant expressing the cystathionine γ-synthase and selecting for progeny expressing the cystathionine γ-synthase and overexpressing feed back insensitive aspartae kinase (AK).

According to still further features in the described preferred embodiments, the methionine related metabolite or derivate is biotin.

According to still further features in the described preferred embodiments the polynucleotide is as set forth in SEQ ID NOs:3 or 4.

According to still further features in the described preferred embodiments one or more of the metabolites, such as, dimethylsulfide, contributes to the scent of a flower of a flowering plant.

According to still further features in the described preferred embodiments the plant is a consumable crop plant whereas increasing the level of methionine increases the level of methionine-rich storage proteins stored by the crop and thus the nutritional value of the crop.

According to yet an additional aspect of the present invention there is provided a nucleic acid construct comprising a polynucleotide encoding a cystathionine γ-synthase, the polynucleotide being mutated in, or lacking, a region encoding an N-terminal portion of the cystathionine γ-synthase, the region being functional in downregulating an activity of the cystathionine γ-synthase in the plant.

According to still further features in the described preferred embodiments the polynucleotide is as set forth in SEQ ID NO: 3 or 4

According to still further features in the described preferred embodiments the nucleic acid construct further comprising a promoter sequence being for directing the expression of a polypeptide from the polynucleotide sequence in a plant.

According to still further features in the described preferred embodiments the promoter is selected from the group consisting of an inducible promoter, a constitutive promoter, a tissue specific promoter and a development regulatable promoter.

According to still further features in the described preferred embodiments the nucleic acid construct further comprising an additional polynucleotide sequence encoding a storage protein.

According to still further features in the described preferred embodiments there is provided a plant transformed with the nucleic acid construct described above.

According to still further features in the described preferred embodiments the nucleic acid construct further comprising an additional polynucleotide encoding a transit peptide, the additional polynucleotide being covalently linked to the polynucleotide encoding the cystathionine γ-synthase.

According to still an additional aspect of the present invention there is provided method of controlling ethylene levels of a plant, the method comprising (a) transforming the plant with a nucleic acid construct including a first polynucleotide region encoding a regulatable promoter being for directing the expression of a second polynucleotide region encoding a cystathionine γ-synthase mutated in, or lacking, an N-terminal portion being functional in downregulating an activity of the cystathionine γ-synthase in the plant; and (b) subjecting the plant to conditions which regulate expression of the cystathionine γ-synthase, thereby controlling ethylene levels of the plant According to still further features in the described preferred embodiments step (a) is effected at a developmental stage of the plant suitable for altering fruit ripening.

According to still further features in the described preferred embodiments the second polynucleotide is as set forth in SEQ ID NO: 4.

The present invention successfully addresses the shortcomings of the presently known configurations by providing a method of generating plants rich in methionine and/or it's metabolites.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2 is a schematic representation depicting the *Arabidopsis* CGS cDNA. TP encodes pea rbcS-3A chloroplast transit peptide, which directs the protein into the chloroplast and is subsequently cleaved. Nucleotides are numbered starting at the ATG initiator codon. The primers (A1-A3) used for the PCR reactions are indicated by arrows.

FIG. 3*a* is a schematic diagram depicting the DNA construct used to express full-length *Arabidopsis* CGS. Abbreviations: PRO: 35S CaMV promoter including sequence encoding Ω mRNA leader; TP: pea rbcS-3A chloroplast transit peptide; 3×HA: haemaglutinin epitope tag; TER: octapine synthase 3' terminator.

FIG. 3*b* is a schematic diagram depicting the DNA construct used to express the 90-bp domain-deleted isoform of *Arabidopsis* CGS (Δ296-386). Abbreviations: PRO: 35S CaMV promoter including sequence encoding Ω mRNA leader; TP: pea rbcS-3A chloroplast transit peptide; 3×HA: haemaglutinin epitope tag; TER: octapine synthase 3' terminator.

FIG. 3*c* is a schematic diagram depicting the DNA construct used to express N-terminal domain-deleted (Δ1-519) *Arabidopsis* CGS. Abbreviations: PRO: 35S CaMV promoter including sequence encoding Ω mRNA leader; TP: pea rbcS-3A chloroplast transit peptide; 3×HA: haemaglutinin epitope tag; TER: octapine synthase 3' terminator.

FIG. 4 is a diagram comparing the amino acid sequences of the CGS enzymes of different organisms. Boxes indicate amino acid residues that are identical (black) or similar (gray). Dashes indicate gaps introduced to optimize the alignment. The N-terminal domain sequences of the CGSs are depicted in pink lettering. Red lettering indicates the 90-bp deleted isoform found in the *Arabidopsis* cDNA (see also FIG. 3*b*). Yellow lettering indicates the point mutations of the MTO1 mutant. The blue letter in the *Arabidopsis* sequence at position 69 indicates the start of the mature protein (Ravanel et al., Biochem J. 1998, 331:639). The CGS sequences compared are from *Glycine max* (soybean, SEQ ID NO:9), *Arabidopsis thaliana* (SEQ ID NO:8) *Zea mays* (SEQ ID NO:10), *Escherichia coli* (SEQ ID NO:11) and *Helicobacter pylori* (SEQ ID NO: 12) GenBank accession nos. AAD34548, U43709, AAB6 1347, P24601, AE000511, respectively. The program ClustalW was used to generate the alignment.

FIG. 5*a* is a diagram depicting the nucleotide sequence of full-length *Arabidopsis* CGS cDNA (SEQ ID NO: 1)

FIG. 5*b* is a diagram depicting the nucleotide sequence of full-length *Arabidopsis* CGS cDNA lacking sequences encoding transit peptide (used in the construct depicted in FIG. 3*a*) (SEQ ID NO: 2).

FIG. 5*c* is a diagram depicting the nucleotide sequence of the 90 bp domain-deleted *Arabidopsis* CGS cDNA (used in the construct depicted in FIG. 3*b*) (SEQ ID NO: 3).

FIG. 5*d* is a diagram depicting the nucleotide sequence of N-terminal domain-deleted *Arabidopsis* CGS cDNA (used in the construct depicted in FIG. 3*c*) (SEQ ID NO: 4).

FIG. 6 depicts Western blot analysis of protein from transgenic plants expressing *Arabidopsis* CGS probed with anti-3HA epitope tag antibodies or CGS antiserum. Protein of transgenic plants expressing: N-terminal domain-deleted CGS (truncated plants, lanes 1-3); the full-length CGS (lanes 4-6); or a 90 bp domain-deleted CGS (deleted, lanes 8-10). WT—wild-type plant. The migration of MW protein markers is indicated on the right.

DESCRIPTION OF THE PREFERRED EMBODIMENTS

Figure 1A:
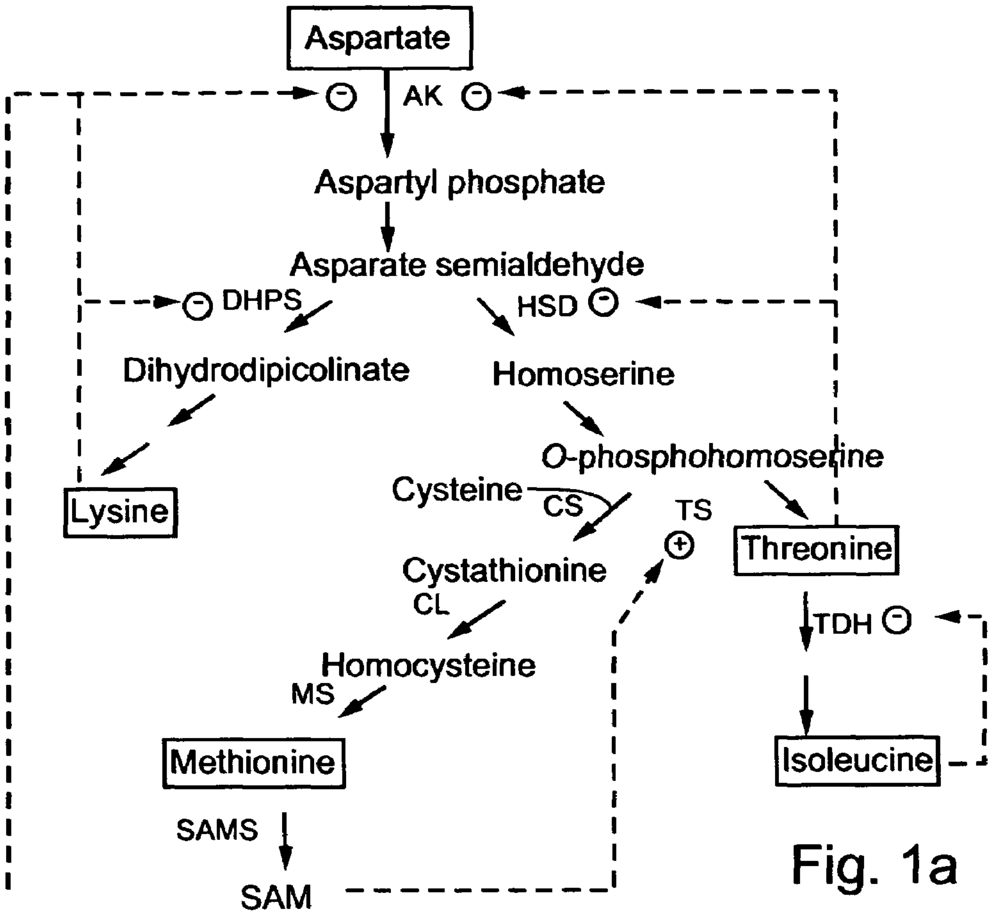
FIG. 1*a* is a diagram depicting biosynthetic pathways of the aspartate family amino acids. Major regulatory enzymes and their products are indicated. Feedback inhibition (−) and activation (+) loops are shown by dashed arrows. Abbreviations: AK=aspartate kinase; DHPS=dihydrodipicolinate synthase; HSD=homoserine dehydrogenase; HK=homoserine kinase; TS=threonine synthase; CGS=cystathione γ-synthase; CL=cystathionine γ-lyase; MS=methionine synthase; TDH=threonine dehydratase; SAM=S-adenosyl methionine; SAMS=SAM synthase.
Figure 1B:
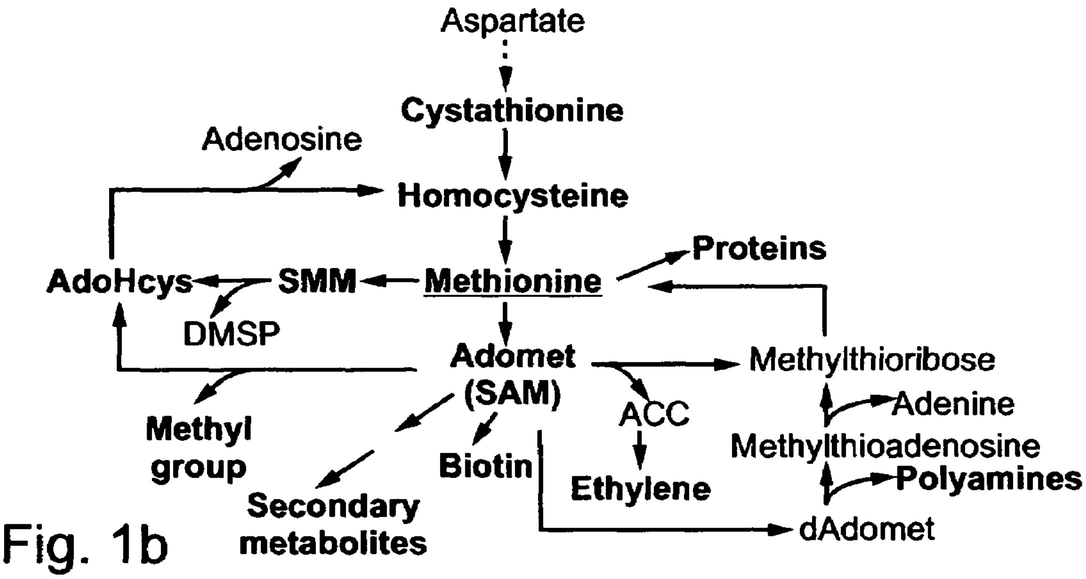
FIG. 1*b* is a diagram depicting methionine metabolism and recycling. Abbreviations: SMM=S-methylmethionine; AdoHCys=S-adenosylhomocysteine; SAM=S-adenosylmethionine; DMSP=3-dimethylsulfoniopropionate; ACC=1-aminocyclopropane-1-carboxylic acid.

The present invention is of a method which can be used to generate is plants rich in methionine and/or methionine related metabolites and of plants generated by this method. Specifically, the present invention can be used to generate crop plants characterized by a higher nutritional value and/or a capacity to accumulate and/or release various compounds derived from methionine.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following descriptions or illustrated in the Examples section. The invention is capable of other embodiments or of being practiced or carried out in various ways. Also, it is to be understood that the phraseology and terminology employed herein is for the purpose of description and should not be regarded as limiting.

The production and accumulation of methionine and it's metabolites in plants is important to both plants and animals which obtain at least a part of their dietary needs from plants.

As used herein the term "plant" refers to whole plants, any plant portion, plant derived material such as mashed, chopped or otherwise processed plant material and plant cells such as plant cells grown in culture.

While reducing the present invention to practice the present inventors have uncovered that transformation of plants with a polynucleotide encoding a truncated cystathionine γ-synthase enzyme results in accumulation of methionine and it's related metabolites in the plant.

As is further described in the Examples section which follows, the plants generated according to the teachings of the present invention exhibit higher levels of methionine, SMM, dimethylsulfide, carbon disulfide, ethylene and biotin than wild type plants or plants expressing full length cystathionine γ-synthase.

Thus, according to one aspect of the present invention, there is provided method of increasing methionine and/or methionine related metabolites in a plant.

The method is effected by expressing within the plant a cystathionine γ-synthase encoded by a polynucleotide mutated in, or lacking, a region encoding an N-terminal portion of the cystathionine γ-synthase, the region being functional in downregulating an activity of the cystathionine γ-synthase in the plant.

Such "downregulating of activity" can result from inhibition of cystathionine γ-synthase activity (e.g., feedback inhibition), inhibition of expression (transcription and/or translation), reduced stability of the mRNA encoding cystathionine γ-synthase, or post transcriptional and/or post translational modifications which result in downregulation of activity. Other mechanisms are also envisaged As is further described in the examples section which follows, such an N-terminal portion encompasses a 90 base pair region which resides downstream of a transit peptide sequence native to plant cystathionine γ-synthase (nucleotide coordinates 296-386 of SEQ ID NO:1).

Thus, any polynucleotide sequence generated by either deleting a portion of this region, the entire region or more, as exemplified by SEQ ID NO: 3 or 4, or by mutating this region in a manner which affects the sequence of the resulting transcript and optionally the sequence of the polypeptide translated therefrom can be utilized by the present invention, as long as cystathionine γ-synthase activity is retained and downregulation of this activity is at least partially abolished when expressed within the plant.

The polynucleotide sequence utilized by the present invention can also include a transit peptide encoding sequence for directing the formed cystathionine γ-synthase to an intracellular compartment (see the Examples section below for further detail).

Preferably, the polynucleotide sequence of the present invention forms a part of a nucleic acid construct which also includes a promoter sequence for directing the expression of cystathionine γ-synthase in a constitutive, tissue specific, inducible or developmentally regulatable manner.

Numerous examples of such promoter sequences are known in the art. Examples of constitutive plant promoters include, without limitation, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

Particularly useful promoters for use in the present invention are tissue-specific promoters such as fruit, flower, tuber or seed specific promoters. There are numerous examples of tissue specific promoters known in the art. Tissue specific promoters may be used according to the present invention to direct methionine overproduction in tissues consumed as food or feed, such as seeds in cereals and tubers in potatoes. Examples of seed-specific promoters include, but are not limited to, the bean phaseolin storage protein promoter shown to be expressed in a seed-specific manner in transgenic tobacco plants [Sengupta-Gopalan, 1985, Proc. Natl. Acad. Sci. USA 82: 3320-3324]; DLEC and PHSβ promoters from *Phaseolus* [Bobb et al., 1997, Nucleic Acids Res. 25: 641-7]; zein storage protein promoter [Vicente-Carbajosa et al., 1997, Proc. Natl. Acad. Sci. USA, 94: 7685-90]; conglutin gamma promoter from soybean [Ilgoutz et al., 1997, Plant Mol Biol 34: 613-27]; AT2S1 gene promoter [Roeckel et al., 1997, Transgenic Res 6: 133-41]; ACT11 actin promoter from *Arabidopsis* [Huang et al., 1997, Plant Mol. Biol. 33: 125-39]; napA promoter from *Brassica napus* [Ellerstrom et al., 1996, Plant Mol Biol 32: 1019-27]. Examples of other fruit or seed specific promoters include the E8, E4, E17 and J49 promoters from tomato [Lincoln and Fischer 1988, Mol Gen Genet 212, 71-75], as well as the 2A11 promoter described in U.S. Pat. No. 4,943,674.

The inducible promoter is a promoter induced by a specific stimuli such as stress conditions including, for example, light, temperature, chemicals, drought, high salinity, osmotic shock, oxidant conditions or by pathogenic attack. Examples of inducible promoters include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

The nucleic acid construct of the present invention preferably further includes additional polynucleotide regions which provide a broad host range prokaryote replication origin; a prokaryote selectable marker; and, for *Agrobacterium* transformations, T DNA sequences for *Agrobacterium*-mediated transfer to plant chromosomes. Where the heterologous sequence is not readily amenable to detection, the construct will preferably also have a selectable marker gene suitable for determining if a plant cell has been transformed. A general review of suitable markers is found in Wilmink and Dons, Plant Mol. Biol. Reptr. (1993) 11:165-185.

Suitable prokaryote selectable markers include resistance toward antibiotics such as ampicillin, kanamycin or tetracycline. Other DNA sequences encoding additional functions may also be present in the nucleic acid construct, as is known in the art.

Sequences suitable for permitting integration of the polynucleotide sequence of the present invention into the plant genome are also recommended. These might include transposon sequences as well as Ti sequences which permit random insertion of a heterologous expression cassette into a plant genome.

Several approaches can be utilized to introduce such polynucleotide sequences into a monocotyledonous or dicotyledonous plant.

The nucleic acid construct of the present invention can be utilized to stably or transiently transform plant cells. In stable transformation, the polynucleotide of the present invention is integrated into the plant genome and as such it represents a stable and inherited trait. In transient transformation, the polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fiber or silicon carbide whisker mediated transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues. In glass fibers or silicon carbide whisker mediated transformation, glass fibers or silicon carbide needles like structures are mixed with DNA and cells in a suspension to thereby induce fiber/whisker-cell collisions, which lead to cell impalement (by the fibers/whiskers) and polynucleotide injection into the cell.

The transformation methods described hereinabove are typically followed by propagation of transformed tissues. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of, for example, flower tissue, leaf tissue, seeds, tubers or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted.

Alternatively, the coat protein gene may be inactivated by insertion of the non-native nucleic acid sequence within it, such that a protein is produced.

The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

As is described in detail in the Examples section which follows, the plants generated according to the teachings of the present invention are characterized by several commercially important traits.

It has been shown that the protein storage capacity of numerous crop plants is limited by a level of methionine found in these plants. Thus, the ability of plants generated according to the teachings of the present invention to accumulate higher levels of methionine enables such plants to generate and accumulate higher levels of proteins thus greatly increasing the nutritional and commercial value of such plants.

To further increase the level of plant expressed proteins, such as, for example, storage proteins (see examples below), transformed plants expressing the truncated or mutated cystathionine γ-synthase can be crossed with plants expressing high levels of a storage protein and a progeny expressing both can be selected.

Alternatively, plants can be co-transformed with a first polynucleotide encoding the truncated or mutated cystathionine γ-synthase of the present invention and a second polynucleotide encoding a storage protein such as, but not limited to, a maize 15 kDa zein protein which contains 12% methionine by weight; a maize 10 kDa zein protein which contains 22% methionine by weight; a Brazil nut seed 2S albumin which contains 24% methionine by weight; a sun flower seed methionine-rich protein, and a rice 10 kDa seed prolamin which contains 25% methionine by weight.

Co-transfection of plants with the first and second polynucleotides can be effected using two nucleic acid constructs each including a specific polynucleotide or alternatively both polynucleotides can be introduced into the plant via a single nucleic acid construct.

Several approaches can be utilized to enable expression of both polynucleotides from a single construct.

The expression of each polynucleotide can be directed by a dedicated promoter or alternatively, the first and second polynucleotide sequences can be transcribed from a single promoter as a polycistronic message. In such a case, the polycistronic sequence also includes an internal ribosome entry site (IRES) to facilitate translation of the downstream polynucleotide sequence.

Still alternatively, the first and second polynucleotide sequences can be translationally fused around a protease cleavage site cleavable by a plant expressed protease, in which case, protease cleavage of the chimeric polypeptide formed would generate the cystathionine γ-synthase and storage protein.

It will be appreciated that expression of mutant or wild-type aspartate kinase (AK) in any of the plants described above can further increase methionine production and accumulation/assimilation and/or storage protein content in such plants.

Expression of aspartate kinase (AK) (preferably a feed back insensitive mutant form) can be achieved by either directly transforming the plants described above with a polynucleotide sequence encoding such an AK, or alternatively by crossing any of the plants described above with a second plant expressing (preferably high levels—over expression) the AK.

Expression of AK would shift the carbon skeleton towards the threonine branch of the aspartate family, and would thus lead to an increase of threonine and methionine synthesis.

In any case, the resulting plants would be able to generate and accumulate high levels of a storage protein or proteins thus greatly increasing the commercial and/or nutritional value of such plants.

It will be appreciated that since such plants can provide a rich source of protein to both animals and humans, they are suitable for cultivation in geographical regions in which both animals and humans suffer from malnutrition, such as the case with third world countries.

The plants of the present invention are also characterized by high levels of methionine related metabolites/derivates such as SMM, dimethylsulfide, carbon disulfide, ethylene and biotin. Such metabolites may be extracted from the plants using methods known to the schooled artisan, such as, but not limited to, solvent extraction, filtration, chromatography, electrophoresis and the like.

As is further described in the Examples section which follows, some or all of these metabolites participate in plant pathogen resistance, allelopathy or scent production.

As such, the plants generated according to the teachings of the present invention, would exhibit increased pathogen resistance, allelopathic capabilities which are important in limiting growth conditions, an increased or altered scent which can lead to an increase in pollination by insects or other vectors and/or an increase in the commercial and/or nutritional value of the plant.

Since expression of the modified cystathionine γ-synthase of the present invention in plants has led to increased levels of ethylene, the nucleic acid constructs of the present invention can also be used to selectively increase ethylene levels in plants for the purposes of, for example, controlling fruit ripening or plant development.

Thus according to another aspect of the present invention there is provided a method of controlling ethylene levels of a plant. The method according to this aspect of the present invention is effected by transforming the plant with a nucleic acid construct including a first polynucleotide region encoding a regulatable promoter (e.g., inducible, tissue specific, developmentally regulated) which serves for directing the expression of a second polynucleotide region encoding a cystathionine γ-synthase mutated in, or lacking, an N-terminal portion being functional in downregulating an activity of the cystathionine γ-synthase in the plant (preferably that encoded by SEQ ID NO:4). Following transformation and generation of seedlings, positive transformants are selected by standard detection methods (e.g., PCR) or by subjecting the seedlings to conditions suitable for inducing expression of the cystathionine γ-synthase and comparing ethylene levels of transgenic seedlings to that of wild type seedlings.

Once a line of transformants is established, the expression of the cystathionine γ-synthase is regulated by either switching expression on and off using inductive conditions (described hereinabove), or the plant is allowed to grow to a desired stage in which expression of the exogenous cystathionine γ-synthase is switched on and ethylene production is increased.

In any case, the above describe methodology can be used to control fruit ripening or plant development, capabilities which are of high commercial importance.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Vector construction: *Arabidopsis* CGS sequences were cloned as follows. Briefly, total RNA from flowers and leaves was extracted with Tri-Reagent (Sigma), according to the protocol provided by the manufacturer. Complementary DNA was synthesized from 1 µg total RNA by AMV reverse transcriptase (Promega, Madison, Wis.) and CGS cDNAs were cloned by PCR using primers listed in Table 1. cDNAs encoding the full-length and the 90-bp deleted CGS (FIG. 2) were amplified, using primers A1 (SEQ ID NO: 5) and A2 (SEQ ID NO: 6) and primers A3 (SEQ ID NO: 7) and A2 (SEQ ID NO: 6), respectively.

TABLE 1

PCR primers

| Primer | Starting nucleotide coordinate (bp's 3' of CGS cDNA ATG initiator codon) | Nucleotide sequence |
| --- | --- | --- |
| A1 | 204 | 5' AGC**ATG**CTCGTCCGTCAGC TGAGCATTAAAGC 3' (SEQ ID NO: 5) |
| A2 | 1692 | 5' ACCCGGGGATGGGCTTCGA GAGCTTGAAG 3' (SEQ ID NO: 6) |
| A3 | 519 | 5' AGC**ATG**CTCAGCTCCGATG GGAGCCTCACTG 3' (SEQ ID NO: 7) |

Primers A1 and A3 encode an SphI restriction site containing an ATG translation-initiation codon, while primer A2 contains a SmaI restriction site. PCR and reverse transcription (RT)-PCR analyses were performed in transfection experiments according to established protocols (Frohman, M. A., "PCR Protocols: A Guide to Methods and Applications", 1990, Academic Press, San Diego). Amplified CGS sequences were cloned into vector pGMT (Promega) and sequenced with an automatic DNA sequencer (Model 373A, Applied Biosystems, Foster City, Calif.).

Polymerase chain reactions were performed using Expend DNA polymerase (Boehringer) and consisted of 30 cycles of the following set of incubations: 1 min./95° C.→1 min./54° C.→1.5 min./72° C. PCR products were ligated into plasmid pGMT and both DNA strands of inserts were sequenced to control for fidelity of amplification. Following digestion with SphI, the PCR-derived inserts were subcloned into SphI-linearized CE vector (Shaul et al., Plant Physiol. 1992, 100:1157; Karchi et al., The Plant J. 1993, 3:721). Vector CE expresses genes in vegetative tissues and targets synthesized protein to plastids. It contains the 35S promoter of cauliflower mosaic virus and the Ϛ-DNA sequence of the coat protein gene of tobacco mosaic virus which encodes a translation-enhancing mRNA leader (Gallie et al., Plant Cell 1989, 1:301). Targeting of expressed protein to plastids is directed via pea rbcS-3A (rubisco) transit peptide (TP) encoded by a sequence inserted between the Ϛ-DNA and CGS coding sequences. The SmaI-digested fragment of vector CE containing the 35S promoter and the rubisco TP and CGS coding sequences was subcloned into SmaI-digested binary Ti plasmid, pZP111 (Hadjukiewicz et al., Plant Mol. Biol. 1994, 25:989), thus generating insert-containing pZP111 constructs. Tang et al. [Tang at al. 2000, Plant J 23:195-203] designed the pZP111 plasmid with SmaI site at the end of its polylinker site, and an epitop tag of a triple haemaglutinin epitope-tag (3×HA), followed by a TGA stop codon and a 3' terminator derived from the octopine synthetase gene of *Agrobacterium tumefaciens*. The SmaI site enables in-frame fusions with the CGS sequences at the 3' end of the insert. Plasmid pZP111 a also provides a gene for kanamycin resistance.

Plant transformation: Insert-containing pZP111 constructs were used to transform *Nicotiana tabacum* cv Samson NN by the leaf-disk protocol (Hosch et al., Science 1985, 227:1229). Transgenic plants were selected on the basis of their ability to regenerate and root on media containing 100 mg/l kanamycin. They were further grown on Nitsch medium in magenta boxes at 25° C., with a light intensity of 30-40 mE m$^{-2}$ sec$^{-1}$ and a 16/8 h day/night regime. Approximately month-old leaves were tested by PCR for the presence of the CGS gene. Thirty transgenic plants from each set of transformations were then transferred to the greenhouse, grown to maturity and selfed.

Western immunoblotting analysis of transgenic protein expression: Leaves were homogenized by mortar and pestle in an equal volume of cold 100 mM Tris-HCl pH 7.5 containing 2 mM EDTA and 1 mM phenylmethylsulfonylfluoride (PMSF). Homogenates were centrifuged (5 min. at 16000 g at 4° C.) and supernatants were harvested. Supernatant proteins were fractionated by SDS-PAGE, transfer-blotted to a PVDF membrane using a Bio-Rad Protein Trans-Blot apparatus and blots were blocked by overnight incubation at 4° C. in a solution containing 5% non-fat milk. Blots were incubated with anti-3HA antibodies or CGS anti-serum for 2 h at room temperature and subsequently incubated with horseradish-peroxidase-conjugated anti-mouse IgG for 2 h at room temperature. Visualization of labeled proteins was performed via an enhanced chemiluminscence immunodetection kit (Pierce), in accordance with the manufacturer's instructions.

Measurement of free amino acid levels in leaves and seeds of transgenic plants: Leaves from approximately month-old, greenhouse-grown tobacco plants were harvested, ground in liquid nitrogen and stored frozen. Free amino acids were extracted from ground and frozen leaves as previously described (Bieleski et al., Anal Biochem. 1966, 17:278). Concentrations of free amino acids were determined using O-phthalaldehyde reagent followed by measurement of 335/447 nm fluorescence. Amino acid composition was determined in samples containing 66 nmol of total free amino acids using a Hewlett-Packard Amino Quant Liquid Chromatograph.

Measurement of protein-bound amino acids levels: Leaves were homogenized and extracted at 4° C. in 100 mM Tris-HCl, pH 7.5 containing 1 mM PMSF and 1 µM leupeptin. Following centrifugation (5 min, 16,000 g, 4° C.) of homogenates, supernatants were collected and protein concentration was determined by the Bradford method. Protein (30 mg) was hydrolyzed in 0.3 ml distilled 6 N HCl at 110° C. for 22 h, under vacuum. The composition of protein-bound amino acids was identified by loading 4 μg of hydrolyzed protein on an HPLC column (Dionex, Bio LC Amino Acid Analyzer).

Gas chromatography and mass spectrometry: The volatile organic compounds (VOCs) from leaves of transgenic plants were determined, using the OI 4560 Purge and Trap system connected to a Hewlett Packard 5890 series II Gas Chromatograph equipped with a 5972 MS Detector. Data analysis was performed using HP MS Chemstation software according to EPA method No 524.2 using 60 m fused silica capillary columns (ID of 0.25 μm and film thickness of 1.4 μm). Double-distilled water (10 ml) was added to 1 g of fresh leaves taken from young transgenic plants, samples were purged at room temperature with 99.999% helium (40 ml per min for 11 min) and VOCs were isolated in an ambient temperature micro-trap containing silica, Tenax and charcoal as adsorbents. Volatile analytes were then thermally desorbed at 180° C. and injected into the gas chromatographic column through a transfer line heated to 100° C. Chromatographic separation was performed over a temperature gradient rising from 35° C. to 220° C. at a rate of 10° C. per minute.

Ethylene production assay: Ethylene production was assayed as previously described (Guzman and Ecker, Plant Cell 1990, 2:513) from young (approximately 10 cm high) regenerated transgenic shoots. Shoots were planted in soil, allowed to grow for three weeks and, were incubated with their pots for 24 h at 22° C. in airtight 1 L magenta. Ethylene was assayed by GC (HP, model 5890) using an Alumina 60/80 column (Model Supleco 020283). An appropriately diluted standard of 640 $\mu l\ L^{-1}$ of ethylene (balance $N_2$) was used to calculate ethylene concentration.

Measurement of biotin: Leaf samples were frozen in liquid nitrogen and biotin levels were measured as previously described (Chang et al., J. Biochem. Biophys. Methods 1994, 29:321) using alkaline phosphatase-conjugated avidin (Extravidin, Sigma) instead of streptavidin-HRP.

Experimental Results

The catalytic domain of CGS is located in the C-terminal domain: Alignment of bacterial and plant CGS sequences reveals that the N-terminal domain of the plant CGS, where the mto1 mutations are located, does not exist in bacterial CGS (FIG. 4). In order to study the role of this domain in *Arabidopsis thaliana* CGS (AtCGS) activity, AtCGS sequences, full-length or containing a deletion of this domain, were cloned into prokaryotic vector pQE (QIAGEN) which was used to transform the CGS-deficient *E. coli* mutant LE392 (metB). As a positive control, the entire open reading frame of *E. coli* CGS was also transformed in the mutant. All of these constructs allowed the mutant to grow on minimal medium lacking Met, whereas vector-only control transformants could not. Therefore, it can be concluded that N-terminal domain-deleted CGS is able to functionally complement the *E. coli* mutant and hence that the catalytic domain of CGS is located in the conserved C-terminal domain of this enzyme. We further suggest that the N-terminal domain of CGS serves an additional plant-specific regulatory role in the function of CGSs.

An alternate transcript of CGS containing a 90 bp in-frame deletion within the N-terminal domain: CGS-encoding DNA was PCR-amplified from an *Arabidopsis* flower cDNA library using primers A1 and A2 (FIG. 2, Table 1). Two amplification products were generated; one with a size corresponding to full-length CGS and the second shorter by about 0.1 kb. The sequence of the longer product was found to correspond to that expected for full-length CGS (Genbank accession number U43709) while the smaller one was found to contain a 90 bp deletion within the N-terminal domain, between nucleotides 296 and 386 (FIG. 2 and at protein level see FIG. 4, red letters). This 90 bp deletion was found to keep the protein sequence in frame, suggesting that protein functionality, including catalytic activity, was retained on the C-terminal side of the deletion. The sequences of the full-length CGS and that of its deleted version are shown in FIG. 5.

Primers A1 and A2 were also employed to amplify CGS cDNA from an *Arabidopsis* hypocotyl cDNA library and, via RT-PCR, from total RNA extracted from *Arabidopsis* leaves, flowers, roots and seedlings. In all cases, both the full-length and the 90 bp domain-deleted cDNA sequences were amplified. Sequence analysis of the *Arabidopsis* database failed to identify a separate CGS gene lacking this 90 bp domain, implying that both the full-length and the deletion-containing cDNAs are produced from the same gene. The 90 bp deletion is contained within exon 1 of the CGS transcript (FIG. 2) and is not flanked by any known consensus intron/exon boundary sequences. Its vicinity to the MTO1 region 45 bases downstream (FIG. 2), which is important for post-transcriptional regulation of CGS levels, suggests that this deleted region may be involved in regulating CGS expression.

Generation of tobacco plants transgenic for deletion mutants of CGS: In order to analyze the role of the deleted 90 bp domain and of the N-terminal domain of CGS in plants, constructs encoding full-length, 90 bp domain-deleted (Δ296-386) and N-terminal domain-deleted (Δ1-519) *Arabidopsis* CGS cDNA were prepared (FIGS. 3*a*, 3*b* and 3*c*, respectively). Since the N-terminal domain-deleted construct does not possess a transit peptide, and to shorten the sequence, the original TP in these constructs has been removed and replaced by pea rbcS-3A TP fused in-frame to the CGS coding sequence. These constructs further comprise an epitope tag (3HA) at their 3' termini, enabling detection of expressed protein by Western blot, distinction of transgenic from endogenous protein and establishment of whether a single DNA or cDNA sequence can give to both the full-length and the 90 bp-deleted isoforms of CGS. Transgenic tobacco plants were generated using these three constructs.

Analysis of tobacco plants transgenic for N-terminal domain-deleted and 90-bp domain-deleted CGS: Transgenic T0 tobacco plants were selected, on sterile media containing 100 mg/l kanamycin sulfate. Thirty kanamycin-resistant plants from each transgenic line were analyzed by PCR for the presence of the CGS transgenes. All plants were found to contain their respective transgenes. Expression of transgenic CGS protein in vegetative tissues of T0 plants was analyzed via Western immunoblotting with anti-3HA antibodies or CGS anti-serum. FIG. 6 show the results of several representative plants expressing the various CGS transgenes. Protein species corresponding in size to the expected forms of CGS were expressed at varying levels, indicating that CGS is processed as it is transported into plastids. In plants expressing high levels of full-length CGS protein, an additional species of a size corresponding to that of the 90 bp-deleted protein was detected, suggesting that both isoforms are transcribed from a single gene.

Phenotype of CGS-transgenic tobacco plants: The phenotype of seven week-old, kanamycin-resistant, greenhouse-grown plants was assessed. Plants transgenic for full-length CGS generally displayed a phenotype similar to wild-type, however plants transgenic for N-terminal-deleted CGS exhibited stunted growth and delayed development, and had narrower, greener and curlier leaves. These characteristics were most noticeable at later stages of plant development. Furthermore, the plants lost their apical dominance, buds formed on primary stems, and displayed bushy structures. Buds were produced in the upper stems but most were cut off following formation of an abscission zone and some, mostly sterile, flowers formed. The life-span of these plants was found to be 2.5 years, a dramatic extension from their normal lifespan of 3-6 months. These plants were perhaps enabled to survive due to their sustained growth of secondary stems.

Most of the transgenic plants expressing the 90 bp-deleted CGS gene exhibited a similar phenotype to those expressing full-length CGS and the wild type plants. However, some of the plants expressing high levels of the 90 bp-deleted transgenic protein were slightly abnormal, exhibiting greener and narrower leaves than the wild-type. This phenotype was diminished in latter developmental stages.

Figure 8A:
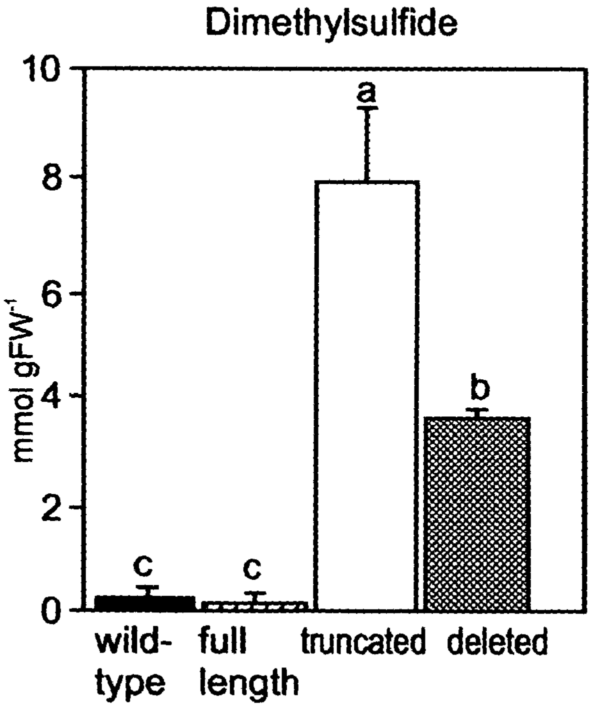
FIGS. 8*a-b* illustrate patterns of volatile organic compounds (VOC) detected from wild-type plant and transgenic plants expressing full-length, truncated and deleted version of CGS. The amount of dimethylsulfide (8*a*) and carbon disulfide (8*b*) emitted from fresh leaves was calculated by determined the area of the corresponding peak in the GC-MS graph as compared to a known standard. The data are presented as the mean±SE (black bars) of eight individual plants, one measurement per plant.
Figure 8B:
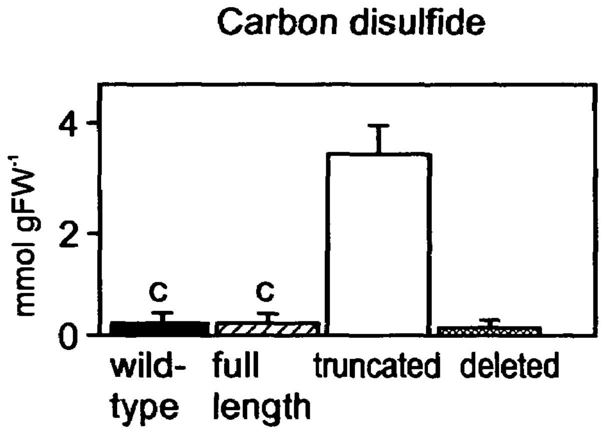

Emmission of dimethyl sulfide from transgenic plants expressing N-terminal domain-deleted CGS: One of the most notable characteristics of transgenic plants expressing the N-terminal-deleted CGS is a typical, very heavy odor. In order to determine the identity of the chemical causing this odor, GC-MS was analysis was performed on 1 g of young leaves as described in the methods section. As shown in FIGS. 8*a-b*, transgenic plants were found to principally emit the VOC dimethylsulfide and carbon disulfide, both catabolic products of Met. In one transgenic plant (N60), emission of dimethylsulfide was found to be 60-fold higher than that in wild-type plants. Although broad variation in dimethylsulfide production was observed overall within the transgenic plants, those expressing N-terminal-deleted CGS were found to produce 21 times the levels of dimethylsulfide as compared to wild-type plants or transgenic plants expressing the full-length CGS (FIGS. 8*a-b*). In most cases a positive correlation was observed between expression levels of CGS, as indicated by Western immunoblot analysis, and dimethylsulfide production levels. In addition, changes in the levels of other compounds such as pentanal, hexanal and hexanol were also observed (Table 2).

Figure 9:
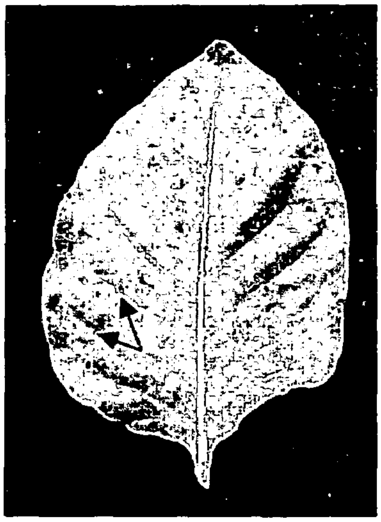
FIG. 9 illustrates attraction of mosquitoes to plants expressing the CGS lacking its N-terminal region.

The heavy odor emitted from plants expressing the CGS lacking its N-terminal region attracted small mosquitoes as shown in FIG. 9.

TABLE 2

Analysis of transgenic plants expressing the *Arabidopsis* CGS cDNA

| Plant ID # | phenotype | western blot | SMM (% free amino acid) | Met (% free amino acid) | Quantity (GCMS results × 103 units) Dimethyl sulfide | Carbon disulfide | Pentanal | Hexanal | Hexanol |
|---|---|---|---|---|---|---|---|---|---|
| N5 | – | + | 0 | 0 | 60 | 110 | 8 | 95 | 15 |
| N11 | + | +++ | 6.2 | 2.9 | 680 | 0 | 0 | 100 | 0 |
| N23 | + | ++ | 7.2 | 0.9 | 230 | 35 | 6 | 12 | 8 |
| N25 | + | +++ | 10.5 | 1.7 | 400 | 190 | 6 | 18 | 11 |
| N37 | + | +++ | 6.9 | 0.9 | 250 | 0 | 30 | 390 | 200 |
| N44 | + | ++ | 6.7 | 1.0 | 530 | 550 | 0 | 48 | 0 |
| N46 | – | ++ | 15.9 | 11.2 | 980 | 0 | 10 | 8 | 0 |
| N63 | + | +++ | 8 | 0.92 | 450 | 220 | 0 | 280 | 144 |
| N66 | + | +++ | 10.4 | 2.7 | 1250 | 0 | 13 | 50 | 35 |
| D40 | + | +++ | 13.8 | 1.8 | 260 | 90 | 10 | 92 | 30 |
| D44 | – | +++ | 16.2 | 1.5 | 240 | 0 | 10 | 38 | 0 |
| D48 | – | + | 5.7 | 0.7 | 160 | 22 | 0 | 62 | 28 |
| D53 | – | +++ | 13.0 | 7.2 | 500 | 38 | 0 | 58 | 36 |
| D55 | – | ++ | 12.4 | 0.5 | 500 | 60 | 8 | 110 | 20 |
| D56 | – | ++ | 9.7 | 2.7 | 48 | 12 | 16 | 100 | 32 |
| D67 | – | +++ | 7.8 | 5.0 | 140 | 0 | 8 | 32 | 0 |
| D70 | + | ++ | 10.5 | 2.5 | 132 | 7 | 17 | 27 | 0 |
| D71 | + | ++ | 9.9 | 1.1 | 240 | 80 | 20 | 134 | 35 |
| D76 | – | ++ | 8.1 | 4.1 | 190 | 18 | 8 | 96 | 0 |
| F23 | – | +++ | 4.9 | 0.3 | 24 | 5 | 8 | 50 | 0 |
| F30 | – | +++ | 5.4 | 1.1 | 130 | 0 | 350 | 130 | 0 |
| F39 | – | +++ | 6.4 | 0.7 | 310 | 59 | 0 | 200 | 32 |
| F41 | – | ++ | 10.8 | 1.9 | 7 | 0 | 34 | 75 | 0 |
| F45 | – | + | 12.5 | 0.6 | 40 | 11 | 0 | 200 | 0 |
| F47 | – | ++ | 10.2 | 1.0 | 9 | 0 | 13 | 131 | 21 |
| F63 | – | ++ | 3.0 | 0.2 | 60 | 0 | 17 | 110 | 0 |
| F66 | – | ++ | 8.9 | 0.5 | 5.5 | 0 | 5 | 27 | 0 |
| F71 | – | +++ | 4.6 | 3.4 | 17 | 0 | 3.5 | 23 | 8.5 |
| NN10 | – | – | 0.8 | 0 | 15 | 5 | 5 | 0 | 22 |
| NN11 | – | – | 1.6 | 0 | 26 | 16 | 8 | 58 | 68 |
| NN12 | – | – | 0.5 | 0.2 | 5 | 55 | 6 | 80 | 0 |

Transgenic lines denoted by N# express N-terminal domain-deleted CGS and those denoted by D# express 90 bp domain-deleted CGS. Transgenic lines expressing full-length CGS are denoted by F#. Wild-type plants are denoted by NN#. Levels of Met and SMM are calculated as % mole from total amino acids. Results from GC-MS analysis are also indicated.

Figure 7A:
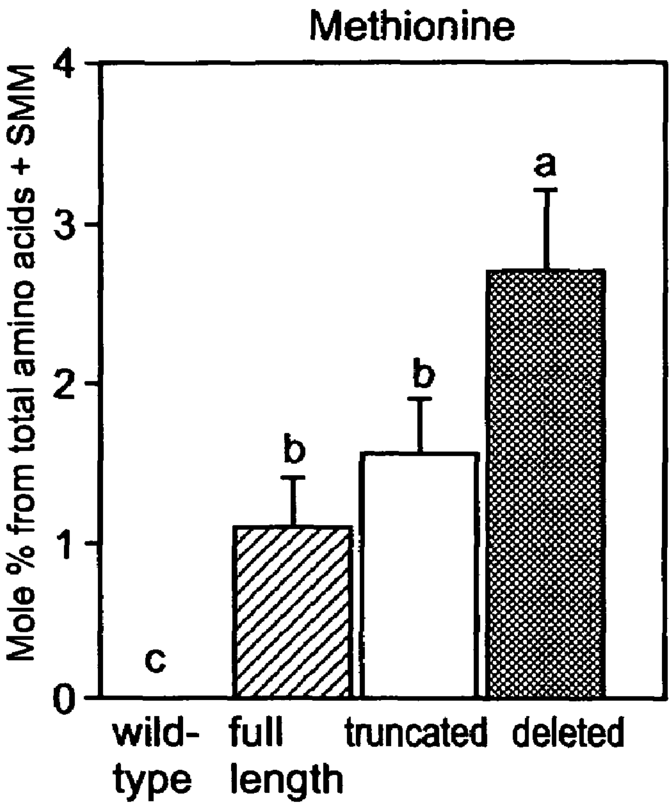
FIGS. 7*a-c* illustrate levels of methionine (7*a*); SMM (7*b*) and methionine incorporated into proteins (7*c*) in wild-type and transgenic lines expressing full-length, truncated and deleted version of *Arabidopsis* CGS. The amounts of methionine and SMM were calculated from total free amino acids plus SMM as detected by HPLC and is indicated as mole % of this total. The methionine level incorporated into proteins was calculated from PBS-soluble proteins that were subjected to amino acid analysis following protein hydrolysis by HPLC. The levels of soluble methionine, SMM and bound methionine were determined from leaf extracts of plants grown for seven weeks. The data are presented as the mean±SE of eight individual plants per line, one measurement per plant. Statistically significant differences ($p<0.05$) are identified by letters.
Figure 7B:
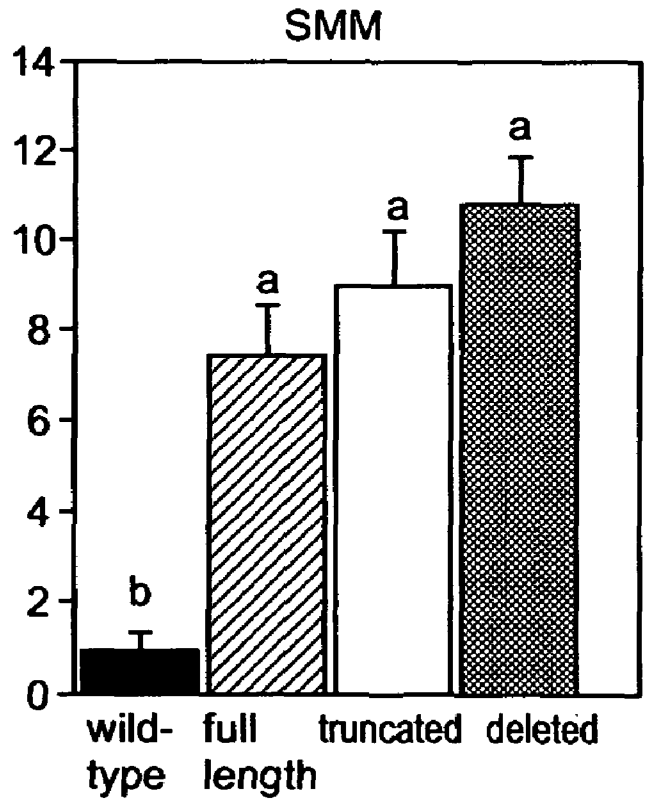

Amino acid analysis of transgenic plants: Free amino acids were extracted from young leaves and levels of Met and SMM, as % total free amino acids, were determined. Levels of Met were found to be higher in all three transgenic lines expressing CGS at moderate to high levels than in the wild-type plants (FIGS. 7*a,b*). The highest levels observed (11.2%, plant N46) represent a 56-fold increase relative to wild-type. Average Met levels were found, in order of decreasing percentage, to be 2.7% in plants expressing 90 bp-deleted CGS, 1.7% in plants expressing N-Terminal-deleted CGS, 1.1% in plants expressing full-length CGS. and 0.1% in wild-type plants. The same general trend was detected in the average SMM levels (FIG. 8b); Overall, levels of SMM in transgenic plants were increased 7- to 16-fold over wild-type plants.

Figure 7C:
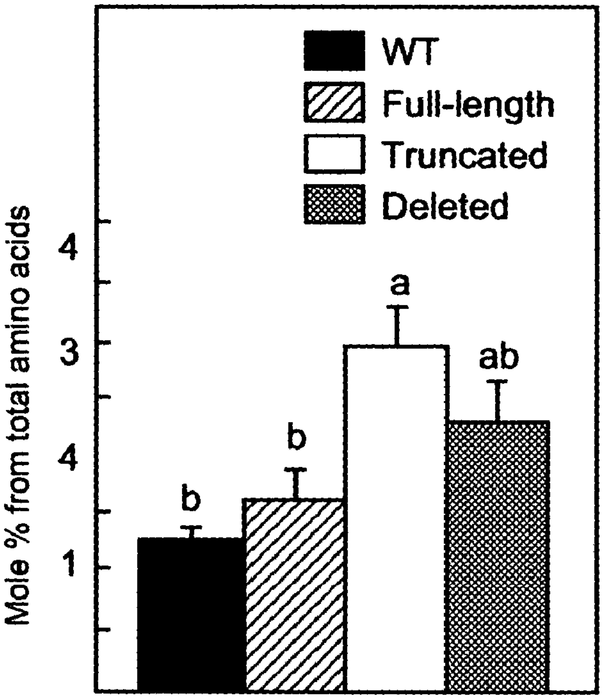

Levels of protein-incorporated Met were also analyzed in leaves of transgenic plants (FIG. 7c). Levels of protein-incorporated Met increased 2-fold in plants expressing N-terminal domain-deleted CGS relative to wild-type. Thus, overexpression of CGS, obtained via deletion of negative regulatory sequences in exon 1, leads to increased levels of Met and SMM production in the transgenic tobacco plants. Importantly, the levels of the other aspartate family amino acids, threonine, lysine and isoleucine, remained unchanged in these plants.

Figure 10:
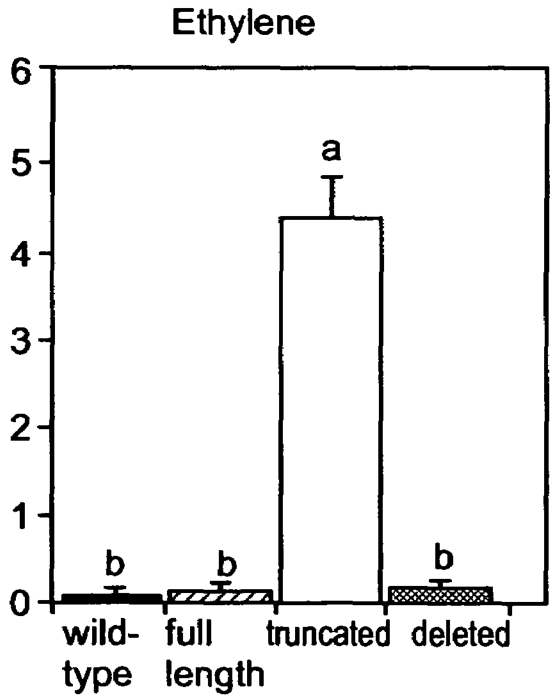
FIG. 10 illustrates ethylene production by three week old shoots of transgenic and wild-type plants. The average±SE of five different shoots is shown.

Ethylene production: Ethylene, one of the major phytohormones in plants, is synthesized from methionine via SAM. Since the transgenic plants expressing the truncated CGS possesed a phenotype that resembles ethylene symptoms, the rate of ethylene emission in three-week-old shoots regenerated from transgenic and wild-type plants was tested. As shown in FIG. 10, ethylene production was comparable between wild-type and transgenic plants expressing full-length and deleted version of *Arabidopsis* CGS. However, in the transgenic plants expressing the tuncated CGS which lacks the N-terminal region, ethylene production was nearly 40 times higher than that of wild-type plants. This high level of ethylene may explain some of the abnormal phenotypes observed in the transgenic plants, such as enhanced abscission of flower buds, dryness of the apical meristem and leaf primordium, retarded stem elongation, as well as curled leaves.

Biotin production: As shown in Table 3, biotin levels in the transgenic plants expressing the N-terminal domain deleted CGS were found to be 20% higher than that of wild-type plants.

TABLE 3

Biotin levels in plants expressing N-terminal domain-deleted CGS versus that in wild-type plants (NN)

| Strains | Picogram biotin/ µg tissue | Wild-type | Picogram biotin/ µg tissue |
|---|---|---|---|
| N13 | 9.45 | NN1 | 10.18 |
| N14 | 9.48 | NN2 | 8.32 |
| N44 | 9.04 | NN3 | 5.35 |
| N46 | 16.29 | NN4 | 8.03 |
| N63 | 10.23 | NN5 | 10.02 |
| Average | 10.9 | Average | 8.5 |
| S.D | 1.37 | S.D | 0.77 |

Discussion

The results presented by this study bring forth evidence that CGS activity is the major rate-limiting step in methionine biosynthesis. In addition, several new findings concerning the regulation of methionine biosynthesis and methionine accumulation and catabolism have also been uncovered by this study.

As shown herein, the N-terminal of CGS, a region not essential for enzymatic activity is important in its regulation. Such regulation may occur at the level of transcript stability, as suggested by Chiba et al. [Chiba et al. (1999) Science 286: 1371-1374], who demonstrated that mutations clustered in small part at this N-terminal region can lead to mRNA stability and thus enhance enzyme activity, or alternatively such regulation can occur at the post translational level.

As described hereinabove, a marked increase of methionine levels was observed in the transgenic tobacco plants overexpressing the truncated CGS. However, methionine related metabolite levels also increased in transgenic plants overexpressing the truncated CGS, implying that methionine levels can not be raised beyond a certain threshold in tobacco plants.

In addition, the transgenic plants of the present invention exhibited a two fold increase in protein-bound methionine. Analysis of the characteristic smell of the transgenic plants overexpressing the truncated CGS revealed that methyl and sulfide groups are emitted from the plants. The fact that dimethylsulfide and carbon disulfide are the major compounds emanating from the plants, at a level more than 60 times that of the wild type plants, suggests that the methionine level is not regulated by the sulfur supply or by the cysteine level.

Although plant CGS lacking an N-terminal is similar to bacterial CGS, overexpression of the bacterial gene would not produce similar results since bacterial CGS enzyme utilizes O-succinylhomoserien rather than O-phosphohomoserine as a substrate in the methionine pathway.

Sulfur Emission:

As mentioned hereinabove, analysis of the characteristic smell of the transgenic plants overexpressing the truncated CGS revealed that methyl and sulfide groups are emitted from the plants.

Several possible functions have been attributed to sulfur emission by plants, including its anti-microbial effect, the discharge of toxic compounds produced in cellular metabolism, or allelopathic effects in plant communities. Dimethylsulfide and methanthiol are a precursors for varieties of phytoalexins that are involved in the defense responses. This compound is induced by attacks by herbivores (including insects), and deters them [Stadler (2000) in: Sulfur Nutrition and Sulfur assimilation in Higher Plants, Paul Haupt, Bern, Switzerland pp. 187-202; Attieh et al. (1995) J. Biol. Chem. 270: 9250-9257].

In addition, it has been suggested that dimethylsulfide contributes to the scent of flowers, and is an important element in the flavor of many vegetables, beer and tea [Mandin et al. (1999) J. Agric Food Chem 47:2355-2359].

Production of SMM:

Analysis of free amino acids extracted from the transgenic tobacco plants revealed a level of S-methylmethionine (SMM) about ten times higher than that found in wild type plants.

SMM has several important functions in plants. It is produced in all flowering plants from methionine, which has a separate mechanism to convert SMM back to methionine. It functions in both storage and transport of labile methyl moieties. It is thought to be the major form of reduced sulfur capable of phloem movement.

In barley for example, SMM stores methyl groups which are converted back to methionine in periods of high metabolism, such as in the early stages of germination [Pimenta et al. (1998) Plant Physiol. 118:431-438]. In wheat, it has been suggested that SMM which is synthesized in leaves translocates to the grains and is recycled to methionine for use in protein synthesis.

SMM is also a precursor for 3-dimethylsulfoniopropionate (DMSP), an osmoprotectant accumulated by certain plants. Salinization generally enhances DMSP accumulation which is an analog of a betaine having a sulfur atom in place of nitrogen and exhibiting osmoprotectant and cryoprotectant properties similar to that of betaines. When nitrogen supply is limited, higher plants and algae may compensate for reduced capacity to synthesize betaines by producing more DMSP [James et al. (1995) Plant Physiol. 108:1439-1448].

Production of SAM:

The level of S-adenosyl methionine (SAM) was not measured in this study, since it is a very unstable compound and as such difficult to measure. however, an increase in the level of SAM products, biotin and ethylene, in the transgenic tobacco plants indicates higher SAM production in the transgenic plants.

SAM serves as a cofactor for a variety of reactions in all living cells. It is the major methyl-group donor in numerous highly specific transmethylation reactions of proteins, lipids, polysaccharides and nucleic acids. These reactions may also play a crucial role in redirecting intermediates toward specific biosynthetic pathways [Belbahri et al. (2000) Biotechnol. Bioeng. 69:11-20]. In tobacco cells, for example, putricine-N-methyltransferase catalyzes the transfer of a methyl group from SAM to an amino-group of puticine, which is the first step in the biosynthesis of tobacco alkaloids. The lack of SAM may affect this metabolic pathway by altering the product quantitatively and qualitatively. Attempts have been made to increase alkaloid contents in tobacco (nicotine and nornicotine), through transgenic cells overexpressing SAM-synthase 1.

Thus, the present invention also provides an alternative approach to increasing SAM and metabolites such as nicotine and nornicotine in plants.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of increasing methionine and/or methionine related metabolites in a plant, the method comprising expressing within the plant an exogenous polypeptide having a cystathionine γ-synthase catalytic activity, said polypeptide having an amino acid sequence corresponding to SEQ ID NO: 8 and further having at least a mutation and/or deletion in a region corresponding to amino acid coordinates 99 to 131 of SEQ ID NO: 8, thereby increasing methionine and/or methionine related metabolites selected from the group consisting of S-methyl methionine, ethylene, dimethylsulfide, carbon disulfide or biotin in said plant as compared to methionine and/or said methionine related metabolites in a similar wild type plant.

2. The method of claim 1, wherein said at least one mutation and/or deletion is a deletion of the region corresponding to amino acid coordinates 99 to 131 of SEQ ID NO: 8.

3. A method of increasing the nutritional value, and/or sulfur emissions of a plant, the method comprising expressing within at least a portion of the plant an exogenous polypeptide having a cystathionine γ-synthase catalytic activity said polypeptide having an amino acid sequence corresponding to SEQ ID NO: 8 and further having at least a mutation and/or deletion in a region corresponding to amino acid coordinates 99 to 131 of SEQ ID NO: 8, thereby increasing the level of methionine and/or metabolites of selected from the group consisting of S-methyl methionine, ethylene, dimethylsulfide, carbon disulfide or biotin, hence increasing the nutritional value, and/or sulfur emissions of the plant as compared to the nutritional value, and/or sulfur emissions of a similar wild type plant.

4. The method of claim 3, wherein said at least one mutation and/or deletion is a deletion of the region corresponding to amino acid coordinates 99 to 131 of SEQ ID NO: 8.

5. The method of claim 3, wherein the plant is a flowering plant, and whereas increasing the level of methionine increases sulfur emissions into the scent of a flower of said flowering plant.

6. The method of claim 3, wherein the plant is a consumable crop plant.

* * * * *